US012661005B2

(12) United States Patent
Hejrati et al.

(10) Patent No.: US 12,661,005 B2
(45) Date of Patent: Jun. 23, 2026

(54) METHODS AND SYSTEMS FOR BIOMARKER IDENTIFICATION AND DISCOVERY

(71) Applicant: Genentech, Inc., South San Francisco, CA (US)

(72) Inventors: Seyed Mohammadmohsen Hejrati, Stanford, CA (US); Heming Yao, Ann Arbor, MI (US); Miao Zhang, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/646,646

(22) Filed: Apr. 25, 2024

(65) Prior Publication Data

US 2024/0293024 A1     Sep. 5, 2024

Related U.S. Application Data

(63) Continuation of application No. PCT/US2022/047944, filed on Oct. 26, 2022.
(Continued)

(51) Int. Cl.
*A61B 3/12* (2006.01)
*A61B 3/00* (2006.01)
(Continued)

(52) U.S. Cl.
CPC .......... *A61B 3/1225* (2013.01); *A61B 3/0025* (2013.01); *A61B 3/102* (2013.01);
(Continued)

(58) Field of Classification Search
CPC .................. A61B 5/7267; A61B 3/102; G06T 2207/20084; G06T 15/08;
(Continued)

(56) References Cited

U.S. PATENT DOCUMENTS 10,074,038 B2 *  9/2018  Hsieh ..................... G06N 3/084
10,354,171 B2 *  7/2019  Hsieh ..................... G06N 3/084
(Continued)

FOREIGN PATENT DOCUMENTS

KR      102 198 395 B1     1/2021
WO      2019/210079 A1     10/2019

OTHER PUBLICATIONS

Selvaraju et al., "Grad-CAM: Visual Explanations from Deep Networks via Gradient-based Localization," Arxiv: 1610.02391, Mar. 21, 2017.
(Continued)

*Primary Examiner* — Oommen Jacob
(74) *Attorney, Agent, or Firm* — Haynes and Boone, LLP

(57) ABSTRACT

Systems and methods for determining the health status of a retina of a subject. An optical coherence tomography (OCT) volume image of a retina of a subject may be received. A health indication output is generated, via a deep learning model, using the OCT volume image. The health indication output indicates a level of association between the OCT volume image and a selected health status category for the retina. A map output for the deep learning model is generated using a saliency mapping algorithm, generating a map output for the deep learning model using a saliency mapping algorithm. The map output indicates a level of contribution of a set of regions in the OCT volume image to the health indication output generated by the deep learning model.

18 Claims, 7 Drawing Sheets

Related U.S. Application Data

(60) Provisional application No. 63/272,060, filed on Oct. 26, 2021.

(51) Int. Cl.
| | |
|---|---|
| *A61B 3/10* | (2006.01) |
| *A61B 5/00* | (2006.01) |
| *G16H 50/30* | (2018.01) |

(52) U.S. Cl.
CPC ........... *A61B 5/7267* (2013.01); *G16H 50/30* (2018.01); *A61B 2576/02* (2013.01)

(58) Field of Classification Search
CPC . G06T 2207/10101; G06T 2207/30041; G06T 7/0012; G06N 20/00
See application file for complete search history.

(56) References Cited

U.S. PATENT DOCUMENTS

| | | | | |
|---|---|---|---|---|
| 2017/0154139 | A1* | 6/2017 | Iorio ...................... | G06N 20/00 |
| 2018/0060512 | A1* | 3/2018 | Sorenson ......... | G06Q 10/06398 |
| 2018/0373980 | A1* | 12/2018 | Huval ...................... | G06N 3/08 |
| 2019/0340753 | A1* | 11/2019 | Brestel ................. | A61B 6/5217 |
| 2020/0191553 | A1* | 6/2020 | Rothberg ............... | H02J 50/10 |
| 2020/0302238 | A1* | 9/2020 | Nguyen .................. | G06F 18/41 |
| 2021/0073986 | A1* | 3/2021 | Kapur ................... | G16H 10/40 |
| 2021/0369195 | A1* | 12/2021 | Russakoff .............. | G16H 30/40 |
| 2024/0293024 | A1* | 9/2024 | Hejrati ................. | G06T 7/0012 |

OTHER PUBLICATIONS

International Search Report and Written Opinion mailed Feb. 8, 2023 in International Application No. PCT/US2022/047944, 10 pages.

Wen et al., "Interpretable Automated Diagnosis of Retinal Disease using Deep OCT Analysis ", https://arxiv.org/ abs/2109.02436v1, Sep. 3, 2021.

Ahnaf et al., "Understanding CNN's Decision Making on OCT-based AMD Detection", 2021 International Conference on Electronics, Communications and Information Technology (ICECIT), IEEE, Sep. 14-16, 2021, pp. 1-4.

International Preliminary Report on Patentability issued Apr. 30, 2024 in International Application No. PCT/US2022/047944, 7 pages.

International Search Report and Written Opinion mailed Aug. 2, 2023 in International Application No. PCT/US2023/021420, 12 pages.

George et al., "3D-CNN for Glaucoma Detection Using Optical Coherence Tomography", 16th European Conference—Computer Vision—ECCV 2020, vol. 7, Dec. 31, 2019, pp. 52-59.

International Preliminary Report on Patentability issued Nov. 7, 2024 in International Application No. PCT/US2023/021420, 8 pages.

Wu et al., "Optical Coherence Tomography-Defined Changes Preceding the Development of Drusen-Associated Atrophy in Age-Related Macular Degeneration," American Academy of Ophthalmology, Ophthalmology, Dec. 2014, vol. 121, No. 12, pp. 2415-2422.

Wu et al., "Prospective Longitudinal Evaluation of Nascent Geographic Atrophy in Age-Related Macular Degeneration," Jun. 2020, American Academy of Ophthalmology, Ophthalmology Retina, vol. 4, No. 6, pp. 568-575.

Wu et al., "Can the Onset of Atrophic Age-Related Macular Degeneration Be an Acceptable Endpoint for Preventative Trials?" Ophthalmologica, International journal of ophthalmology, Dec. 2020, vol. 243, Issue 6, pp. 399-403.

Derradji et al., "Fully-automated atrophy segmentation in dry age-related macular degeneration in optical coherence tomography." Nov. 8, 2021, Scientific Reports, 11(1), Article 21893.

Corradetti et al., "Automated Identification of Incomplete and Complete Retinal Epithelial Pigment and Outer Retinal Atrophy Using Machine Learning." Investigative Ophthalmology and Visual Science, Jun. 2022, vol. 63, No. 7, 3860.

Chiang et al., "Automated Identification of Incomplete and Complete Retinal Epithelial Pigment and Outer Retinal Atrophy Using Machine Learning." American Academy of Ophthalmology, Ophthalmology Retina, Feb. 2023, vol. 7, No. 2, pp. 118-126.

Yang et al., "Weakly supervised lesion localization for age-related macular degeneration detection using optical coherence tomography images." PLOS ONE, Apr. 5, 2019, 14(4);e0215076.

Selvaraju et al., "Grad-CAM: Visual Explanations from Deep Networks via Gradient-Based Localization." International Journal of Computer Vision, 2020, vol. 128, pp. 336-359.

Shi et al., "Improving Interpretability in Machine Diagnosis: Detection of Geographic Atrophy in OCT Scans," American Academy of Ophthalmology, Ophthalmology Science, Sep. 2021, vol. 1, No. 3, 9 pages.

Yoon et al., "Optical coherence tomography-based deep-learning model for detecting central serous chorioretinopathy." Scientific reports, 2020, vol. 10(1), 18852, 9 pages.

Wang et al., "Explainable Deep Learning for Biomarker Classification of OCT Images." 2020 IEEE 20th International Conference on Bioinformatics and Bioengineering (BIBE), Cincinnati, Ohio, pp. 204-210.

Li et al., "Development and validation of a deep learning system to screen vision-threatening conditions in high myopia using optical coherence tomography images." 2022, The British Journal of Ophthalmology, vol. 106, No. 5, pp. 633-639.

Guymer et al., "Subthreshold Nanosecond Laser Intervention in Age-Related Macular Degeneration: The LEAD Randomized Controlled Clinical Trial." Jun. 2019, American Academy of Ophthalmology, Ophthalmology, vol. 126, No. 6, pp. 829-838.

Wu et al., "Predicting progression of age-related macular degeneration using optical coherence tomography and fundus photography." Feb. 2021, Ophthalmology Retina, vol. 5, No. 2, pp. 118-125.

Guymer et al., "Incomplete Retinal Pigment Epithelial and Outer Retinal Atrophy in Age-Related Macular Degeneration: Classification of Atrophy Meeting Report 4." Mar. 2021, Ophthalmology, vol. 127, No. 3, pp. 394-409.

Carbonneau et al., "Multiple instance learning: A survey of problem characteristics and applications." May 2018, Pattern Recognition, vol. 77, pp. 329-353.

Otsu et al., "A Threshold Selection Method from Gray-Level Histograms." Jan. 1979, IEEE Transactions on Systems, Man, and Cybernetics, vol. SMC-9, No. 1, pp. 62-66.

Liu et al., "A comparison of deep learning performance against health-care professionals in detecting diseases from medical imaging: a systematic review and meta-analysis." Oct. 2019, The Lancet Digital Health, vol. 1, No. 6, pp. e271-e297.

Redmon et al., "YOLOv3: An Incremental Improvement." Apr. 8, 2018. arXiv preprint arXiv:1804.02767.

Holz et al., "Geographic atrophy: Clinical features and potential therapeutic approaches." May 2014. Ophthalmology, vol. 121, No. 5, pp. 1079-1091.

Areds, "A randomized, placebo-controlled, clinical trial of high-dose supplementation with vitamins C and E, beta carotene and zinc for age-related macular degeneration and vision loss. Areds Report No. 8." Archives of Ophthalmology, Oct. 2001, vol. 119, No. 10, pp. 1417-1436.

AREDS 2, "Lutein + Zeaxanthin and Omega-3 Fatty Acids for Age-Related Macular Degeneration." May 15, 2013, JAMA, vol. 309, No. 19, pp. 2005-2015.

Lazaridis et al., "OCT Signal Enhancement with Deep Learning." May-Jun. 2021. Ophthalmology Glaucoma, vol. 4, Issue 3, pp. 295-304.

Wu et al., "Fundus autofluorescence characteristics of nascent geographic atrophy in age-related macular degeneration." Mar. 2015, Retina, Investigative Ophthalmology & Visual Science, vol. 56, No. 3, pp. 1546-1552.

Wu et al., "Microperimetry of nascent geographic atrophy in age-related macular degeneration." Jan. 2015. Investigative Ophthalmology & Vision Science, vol. 56, No. 1, pp. 115-121.

(56)                References Cited

OTHER PUBLICATIONS

Ferrara et al., "Optical coherence tomography features preceding the onset of advanced age-related macular degeneration." Jul. 2017. Investigative Ophthalmology & Vision Science, vol. 58, No. 9, pp. 3519-3529.

Ting et al., "Development and validation of a deep learning system for diabetic retinopathy and related eye diseases using retinal images from multiethnic populations with diabetes." Dec. 12, 2017. JAMA, vol. 318, No. 22, pp. 2211-2223.

Bellemo et al., "Artificial intelligence using deep learning to screen for referable and vision-threatening diabetic retinopathy in Africa: A clinical validation study." May 2019. The Lancet Digital Health, vol. 1, pp. e35-e44.

Abramoff et al., "Pivotal trial of an autonomous ai-based diagnostic system for detection of diabetic retinopathy in primary care offices." Aug. 28, 2018. npj Digital Medicine, vol. 1, No. 1, Article 39, 8 pages.

Ruamviboonsuk et al., "Real-time diabetic retinopathy screening by deep learning in a multisite national screening programme: A prospective interventional cohort study." Apr. 2022. The Lancet Digital Health, vol. 4, pp. e235-e244.

Keenan et al., "A deep learning approach for automated detection of geographic atrophy from color fundus photographs." Nov. 2019. Ophthalmology, vol. 126, Issue 11, pp. 1533-1540.

Goh et al., "Hyporeflective cores within drusen: Association with progression of age-related macular degeneration and impact on visual sensitivity." Apr. 2022. Ophthalmology Retina, vol. 6, No. 4, pp. 284-290.

Goh et al., "Cuticular drusen in age-related macular degeneration: Association with progression and impact on visual sensitivity." Jun. 2022. Ophthalmology, vol. 129, No. 6, pp. 653-660.

Wu et al., "Secondary and exploratory outcomes of the subthreshold nanosecond laser intervention randomized trial in age-related macular degeneration: A Lead study report." Dec. 2019. Ophthalmology Retina, vol. 3, No. 12, pp. 1026-1034.

Ferris et al., "Clinical classification of age-related macular degeneration." Apr. 2013. Ophthalmology, vol. 120, Issue 4, pp. 844-851.

Sadda et al., "Consensus definition for atrophy associated with age-related macular degeneration on OCT: Classification of Atrophy Report 3." Apr. 2018. Ophthalmology, vol. 125, Issue 4, pp. 537-548.

Davis et al., "The age-related eye disease study severity scale for age-related macular degeneration: AREDS Report No. 17." Nov. 2005. Archives of Ophthalmology, vol. 123, No. 11, pp. 1484-1498.

Kumar et al., "A clinical perspective on the expanding role of artificial intelligence in age-related macular degeneration." Jan. 24, 2022. Clinical and Experimental Optometry, vol. 105, No. 7, pp. 674-679.

Wu et al., "Incomplete retinal pigment epithelial and outer retinal atrophy: longitudinal evaluation in age-related macular degeneration." Feb. 2023. Ophthalmology, vol. 130, No. 2, pp. 205-212.

Lee et al., "How Artificial Intelligence Can Transform Randomized Controlled Trials." 2020. Translational Vision Science & Technology, vol. 9, No. 2, Article 9, 4 pages.

Loo et al., "Beyond Performance Metrics: Automatic Deep Learning Retinal OCT Analysis Reproduces Clinical Trial Outcome." Jun. 2020. Ophthalmology, vol. 127, Issue 6, pp. 793-801.

* cited by examiner

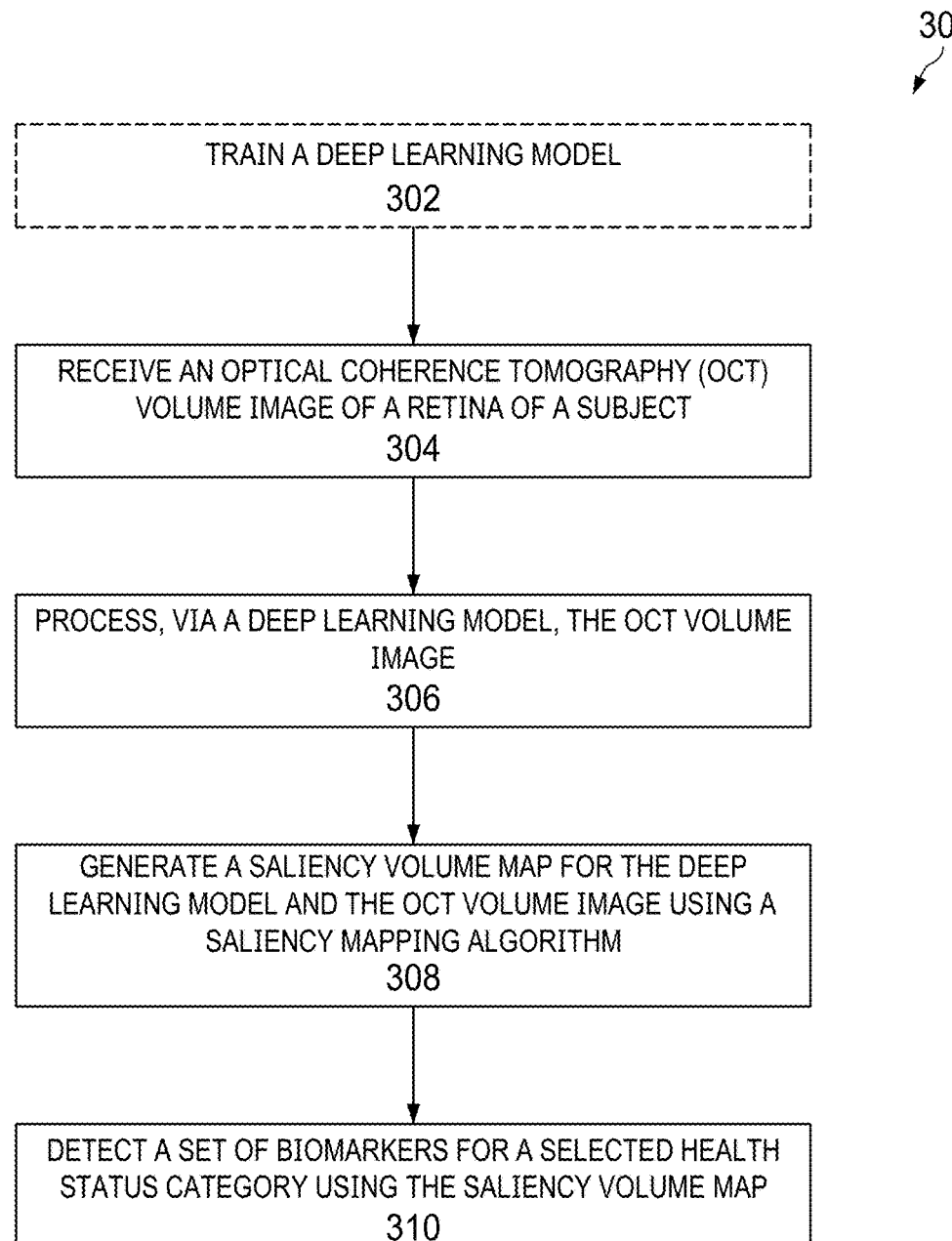

300

TRAIN A DEEP LEARNING MODEL
302

RECEIVE AN OPTICAL COHERENCE TOMOGRAPHY (OCT)
VOLUME IMAGE OF A RETINA OF A SUBJECT
304

PROCESS, VIA A DEEP LEARNING MODEL, THE OCT VOLUME
IMAGE
306

GENERATE A SALIENCY VOLUME MAP FOR THE DEEP
LEARNING MODEL AND THE OCT VOLUME IMAGE USING A
SALIENCY MAPPING ALGORITHM
308

DETECT A SET OF BIOMARKERS FOR A SELECTED HEALTH
STATUS CATEGORY USING THE SALIENCY VOLUME MAP
310

Figure 3

METHODS AND SYSTEMS FOR BIOMARKER IDENTIFICATION AND DISCOVERY

CROSS-REFERENCE TO RELATED APPLICATION

This application is a continuation of International Application No. PCT/US2022/047944 filed Oct. 26, 2022 and entitled "Methods And Systems For Biomarker Identification And Discovery," which claims priority to U.S. Provisional Patent Application No. 63/272,060 filed Oct. 26, 2021 and entitled "Methods and Systems for Biomarker Identification and Discovery," each of which is incorporated herein by reference in its entirety.

FIELD

The present disclosure generally relates to the analysis of optical coherence tomography (OCT) images of retinas and more specifically, to the use of deep learning models to identify current and/or predict future health status and the use of saliency mapping algorithms to identify biomarkers in OCT images that indicate current retinal health status and/or that are prognostic for future retinal health status.

BACKGROUND

Various imaging techniques have been developed to capture medical images of tissues, which may then be analyzed to determine the presence or progression of diseases. For example, optical coherence tomography (OCT) refers to a technique where light waves are used to capture two-dimensional slice images and three-dimensional volume images of tissues such as retinas of patients, which may then be analyzed to diagnose, monitor, treat, etc., the patients. However, the analyses of such images, which may include a large amount of data, are performed manually, and usually by subject matter experts, and as such can be cumbersome and very expensive. Thus, it may be desirable to have methods and systems that facilitate the consistent, accurate, and quick analyses of large amounts of medical images such as OCT images for use in the diagnosis, monitoring and treatment of patients.

SUMMARY

The following summarizes some embodiments of the present disclosure to provide a basic understanding of the discussed technology. This summary is not an extensive overview of all contemplated features of the disclosure and is intended neither to identify key or critical elements of all embodiments of the disclosure nor to delineate the scope of any or all embodiments of the disclosure. Its sole purpose is to present some concepts of one or more embodiments of the disclosure in summary form as a prelude to the more detailed description that is presented later.

In one or more embodiments, a method is provided for receiving an optical coherence tomography (OCT) volume image of a retina of a subject. A health indication output is generated, via a deep learning model, using the OCT volume image in which the health indication output indicates a level of association between the OCT volume image and a selected health status category for the retina. A map output is generated for the deep learning model using a saliency mapping algorithm. The map output indicates a level of contribution of a set of regions in the OCT volume image to the health indication output generated by the deep learning model.

In one or more embodiments, a method is provided for receiving an optical coherence tomography (OCT) volume image of a retina of a subject. A health indication output is generated, via a deep learning model, using the OCT volume image in which the health indication output indicates a level of association between the OCT volume image and a selected health status category for the retina. A saliency volume map is generated for the OCT volume image using a saliency mapping algorithm. The saliency volume map indicates a level of contribution of a set of regions in the OCT volume image to the health indication output generated by the deep learning model. A set of biomarkers in the OCT volume image for the selected health status category is detected using the saliency volume map.

In one or more embodiments, a system comprises a non-transitory memory; and a hardware processor coupled with the non-transitory memory. The hardware processor is configured to read instructions from the non-transitory memory to cause the system to: receive an optical coherence tomography (OCT) volume image of a retina of a subject; generate, via a deep learning model, a health indication output using the OCT volume image in which the health indication output indicates a level of association between the OCT volume image and a selected health status category for the retina; and generate a map output for the deep learning model using a saliency mapping algorithm, wherein the map output indicates a level of contribution of a set of regions in the OCT volume image to the health indication output generated by the deep learning model.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 3 is a flowchart of a process for identifying biomarkers in an OCT volume image of a retina of a subject in accordance with various embodiments.

Figure 1:
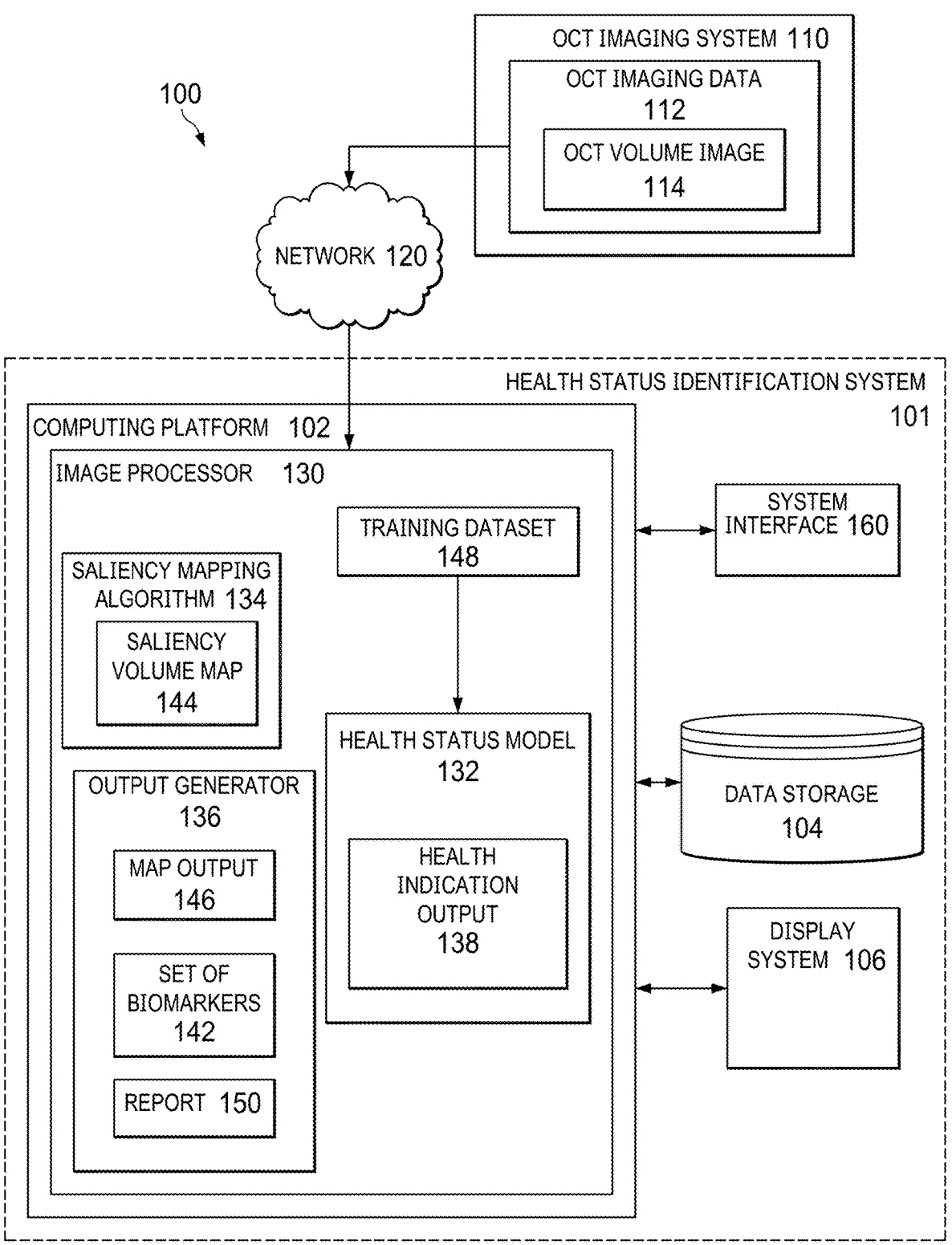
FIG. 1 is a block diagram of a networked system 100 in accordance with one or more embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

I. Overview

Medical imaging technologies are powerful tools that can be used to produce medical images that allow healthcare practitioners to better visualize and understand the medical issues of their patients, and as such provide the same more accurate diagnoses and treatment options. For example, optical coherence tomography (OCT) is a noninvasive imaging technique that is particularly popular for capturing images of the retina. OCT may be described as an ultrasonic scanning technique that scatters light waves from tissues to generate OCT images in the form of two-dimensional (2D) images and/or three-dimensional (3D) images of the tissues, similar to ultrasound scans that use sound waves to scan tissues. A 2D OCT image may also be referred to as an OCT slice, OCT cross-sectional image, or OCT scan (e.g., OCT B-scan). A 3D OCT image may be referred to as an OCT volume image and may be comprised of many OCT slice images. OCT images may then be used for the diagnosis, monitoring and/or treatment of patients from whom the images are obtained. For example, OCT slice images and OCT volume images of the retinas of a patient with age-related macular degeneration (AMD) may be analyzed to provide AMD diagnoses and treatment options to the patient.

Although OCT images of retinas may contain valuable information about patients' ophthalmological conditions, extracting the information from the OCT images can be a resource-intensive and difficult task, leading to erroneous conclusions to be drawn about the information contained in the OCT images. For example, when treating a patient with an eye disease such as AMD, a large set of OCT slices of the retinas of the patient may be obtained, and a set of trained human reviewers may be tasked with manually identifying biomarkers of AMD in the set of OCT slices. Such a process, however, can be cumbersome and challenging, leading to slow, inaccurate, and/or variable identification of biomarkers of retina diseases. Although subject matter experts who are trained at reviewing OCT images may be used to improve the accuracy of biomarker identifications, the process may still be laborious, may have inherent undesirable variability between reviewers, and may be particularly costly. Accordingly, relying on such subject matter experts to review such large sets of OCT slices may not provide health care providers with the efficient, cost-effective, consistent, and accurate mechanism desired for identifying biomarkers of diseases such as AMD. Further, manual review of OCT images may be even less successful at discovering new biomarkers that are prognostic of the future development of retina diseases.

For example, geographic atrophy (GA) may be a late-stage, vision-threatening complication of AMD. While color fundus photography (CFP) or fundus autofluorescence (FAF) can be used to identify GA, there may already be substantial loss of outer retinal tissue by the time a subject matter expert is able to see evidence of GA on these types of images. Determining ways in which to slow or prevent the onset of GA in the early stages of AMD may benefit from identifying early signs or predictors of GA onset. For example, biomarkers for early identification and/or prediction of GA onset can be used to identify high-risk individuals to enrich clinical trial populations, serve as biomarkers for different stages of AMD progression, and/or potentially act as an earlier endpoint in clinical trials aiming to prevent the onset of GA.

OCT images have been used to identify nascent geographic atrophy (nascent GA or nGA), which may be a strong predictor that the onset of GA is near (e.g., within 6-30 months). For example, in some cases, retinas that show nascent GA in OCT images have greater than a 70-fold increased risk of developing GA as compared to those retinas that do not show nascent GA. Thus, nascent GA may be prognostic indicator of a progression from early AMD to GA. Examples of the anatomic biomarkers that define nascent GA in OCT images include, but are not limited to, subsidence of the inner nuclear layer (INL) and outer plexiform layer (OPL), hyporeflective wedge-shaped bands within Henle's fiber layer, or both.

The accurate identification of nascent GA could improve the feasibility of evaluating preventative treatments for the onset of GA. However, manual grading of numerous individual OCT slice images (or B-scans) in an OCT volume image is labor intensive, time-consuming, and consequently, expensive. This is especially the case when a large number of B-scans are acquired per OCT volume image to provide a high spatial resolution when imaging the retina.

Thus, the embodiments described herein provide artificial intelligence (AI)-based systems and methods for quickly, efficiently, and accurately detecting whether an OCT volume image of a retina evidences a selected health status category for the retina. The selected health status category may be, for example, a retinal disease (e.g., AMD) or a stage of retinal disease. In one or more embodiments, the selected health status category is nascent GA. In other embodiments, the selected health status category may be another stage of AMD progression (e.g., early AMD, intermediate AMD, GA, etc.). A deep learning model may be trained to receive an OCT volume image and generate a health indication output that indicates whether the OCT volume image evidences a selected health status category (e.g., nascent GA) for the retina. For example, the health indication output may indicate a level of association between the OCT volume image and the selected health status category. This level of association may be no association, some association, or a full association. The deep learning model may include, for example, a neural network model. As one non-limiting example, the deep learning model may generate a health indication output that is a probability (e.g., between 0.00 and 1.00) that indicates the level of association between the OCT volume image and the selected health status category.

Further, the systems and methods described herein may be used to quickly, efficiently, and accurately identify biomarkers of retina diseases and/or prognostic biomarkers of future retinal disease developments. For example, the systems and methods described herein may be used to identify a set of biomarkers in an OCT volume image that indicate or otherwise correspond to the selected health status category. The systems and methods may also be used to identify a set of prognostic biomarkers in the OCT volume image that are prognostic for the selected health status category (e.g., a progression to the selected health status category within a selected period of time).

In one or more embodiments, a health status identification system that includes a deep learning model is used to process OCT volume images. The health identification system uses the deep learning model, which may include a neural network model, to generate a health indication output that indicates whether an OCT volume image evidences a selected health status category. In some instances, the selected health status category may be one out of a group of health status categories of interest. In one or more embodiments, the selected health status category is a selected stage of AMD. The selected stage of AMD may be, for example, nascent GA.

In one or more embodiments, the health status identification system uses a saliency mapping algorithm (also referred to as a saliency mapping technique) to generate a map output for the deep learning model that indicates whether a set of regions in the OCT volume image is associated with the selected health status category. The saliency mapping algorithm may be used to identify a level of contribution (or a degree of importance) of various portions of the OCT volume image to the health indication output generated by the deep learning model for the given OCT volume image. The health status identification system may use the map output to identify biomarkers in the OCT volume image. A biomarker may indicate that the OCT volume image currently evidences the selected health status category for the retina. In some instances, a biomarker may be prognostic in that it indicates that the OCT volume image is prognostic for the retina progressing to the selected health tatus category within a selected period of time (e.g., 6 months, 1 year, 2 years, 3 years, etc.).

The saliency mapping algorithm described above may be implemented in various ways. One example of a saliency mapping algorithm is gradient-weighted Class Activation Mapping (Grad-CAM), a technique that provides "visual explanations" in the form of heatmaps for the decisions that a deep learning model makes when performing predictions. That is, Grad-CAM may be implemented for a trained deep learning model to generate saliency maps or heatmaps of OCT slice images in which the heatmaps indicate (e.g., using colors, outlines, annotations, etc.) the regions or locations of the OCT slice images that the neural network model uses in making determinations and/or predictions about stages of disease for the retinas shown in the OCT slice images. In one or more embodiments, Grad-CAM may determine the degree of importance of each pixel in an OCT slice image to the health indication output generated by the deep learning model. Additional details about Grad-CAM may be found in R. R. Selvaraju et al., "Grad-CAM: Visual Explanations from Deep Networks via Gradient-based Localization," Arxiv: 1610.02391 (2017), which is incorporated by reference herein in its entirety. Other non-limiting examples of saliency mapping techniques include class activation mappings (CAMs), SmoothGrad, the Low-Variance Gradient Estimator for Variational Inference (VarGrad), and/or the like.

The saliency map generated by the saliency mapping algorithm may then be used to localize one or more potential biomarkers on a given OCT slice image. For example, the saliency map may be used to generate a bounding box around each potential biomarker or potential biomarker region in the OCT slice image. Thus each bounding box may localize the potential biomarker. In one or more embodiments, a scoring metric (e.g., confidence score) may be used to determine which bounding boxes are or contain one or more biomarkers for a selected health status category.

Using the health status identification system with the deep learning model and the saliency mapping algorithm to classify retinal health status and identify biomarkers for a selected health status category in an OCT volume image may reduce the time and cost associated with evaluating the retinas of subjects, and may improve the efficiency and accuracy with which diagnosis, monitoring, and/or treatment can be implemented. Further, using the embodiments described herein may allow subjects to be added to clinical trials at earlier stages of their AMD progression and may improve the informative potential of such clinical trials. Still further, using the embodiments described herein may reduce the overall computing resources used and/or speed up a computer's performance with respect to classifying retinal health status, predicting future retinal health status, and/or identifying biomarkers for a selected health status category.

II. Exemplary Health Status Identification System

FIG. 1 is a block diagram of a networked system 100 in accordance with one or more embodiments. Networked system 100 may include any number or combination of servers and/or software components that operate to perform various processes related to the capturing of OCT volume images of tissues such as retinas, the processing of OCT volume images via a deep learning model, the processing of OCT volume images using a saliency mapping algorithm, the identification of biomarkers that indicate current retinal health status or are prognostic of retinal health status, or a combination thereof. Exemplary servers may include, for example, stand-alone and enterprise-class servers operating a server OS such as a MICROSOFT™ OS, a UNIX™ OS, a LINUX™ OS, or other suitable server-based OS. It can be appreciated that the servers used in networked system 100 may be deployed in other ways and that the operations performed and/or the services provided by such servers may be combined or separated for a given implementation and may be performed by a greater number or fewer number of servers. One or more servers may be operated and/or maintained by the same or different entities.

The networked system 100 includes health status identification (HSI) system 101. The health status identification system 101 may be implemented using hardware, software, firmware, or a combination thereof. In one or more embodiments, the health status identification system 101 may include a computing platform 102, a data storage 104 (e.g., database, server, storage module, cloud storage, etc.), and a display system 106. Computing platform 102 may take various forms. In one or more embodiments, computing platform 102 includes a single computer (or computer system) or multiple computers in communication with each other. In other examples, computing platform 102 takes the form of a cloud computing platform, a mobile computing platform (e.g., a smartphone, a tablet, etc.), or a combination thereof.

Data storage 104 and display system 106 are each in communication with computing platform 102. In some examples, data storage 104, display system 106, or both may be considered part of or otherwise integrated with computing platform 102. Thus, in some examples, computing platform 102, data storage 104, and display system 106 may be separate components in communication with each other, but in other examples, some combination of these components may be integrated together.

The networked system 100 may further include OCT imaging system 110, which may also be referred to an OCT scanner. OCT imaging system 110 may generate OCT imaging data 112. OCT imaging data 112 may include OCT volume images (i.e., 3D OCT images) and/or OCT slice images (i.e., 2D OCT images). For example, OCT imaging data 112 may include OCT volume image 114. The OCT volume image 114 may be comprised of a plurality (e.g., 10s, 100s, 1000s, etc.) of OCT slice images. An OCT slice image may also be referred to as an OCT B-scan or a cross-sectional OCT image.

In one or more embodiments, the OCT imaging system 110 includes an optical coherence tomography (OCT) system (e.g., OCT scanner or machine) that is configured to generate OCT imaging data 112 for the tissue of a patient. For example, OCT imaging system 110 may be used to generate OCT imaging data 112 for the retina of a patient. In some instances, the OCT system can be a large tabletop configuration used in clinical settings, a portable or hand-held dedicated system, or a "smart" OCT system incorporated into user personal devices such as smartphones. The OCT imaging system 110 may include an image denoiser that is configured to remove noise and other artifacts from a raw OCT volume image to generate the OCT volume image 114.

The health status identification system 101 may be in communication with OCT imaging system 110 via network 120. Network 120 may be implemented using a single network or multiple networks in combination. Network 120 may be implemented using any number of wired communications links, wireless communications links, optical communications links, or combination thereof. For example, in various embodiments, network 120 may include the Internet or one or more intranets, landline networks, wireless networks, and/or other appropriate types of networks. In another example, the network 120 may comprise a wireless telecommunications network (e.g., cellular phone network) adapted to communicate with other communication networks, such as the Internet.

The OCT imaging system 110 and health status identification system 101 may each include one or more electronic processors, electronic memories, and other appropriate electronic components for executing instructions such as program code and/or data stored on one or more computer readable mediums to implement the various applications, data, and steps described herein. For example, such instructions may be stored in one or more computer readable media such as memories or data storage devices (e.g., data storage 104) internal and/or external to various components of networked system 100, and/or accessible over network 120. Although only one of each of OCT imaging system 110 and the health status identification system 101 is shown, there can be more than one of each in other embodiments.

In some embodiments, the OCT imaging system 110 may be maintained by an entity that is tasked with obtaining OCT imaging data 112 for tissue samples of subjects for the purposes of diagnosis, monitoring, treatment, research, clinical trials, and/or the like. For example, the entity can be a health care provider (e.g., ophthalmology healthcare provider) that seeks to obtain OCT imaging data for a retina of a patient for use in diagnosing eye conditions or diseases (e.g., AMD) the patient may have. As another example, the entity can be an administrator of a clinical trial that is tasked with collecting OCT imaging data for retinas of subjects to monitor changes to the retinas as a result of the progression/regression of diseases affecting the retinas and/or effects of drugs administered to the subjects to treat the diseases. It is to be noted that the above examples are non-limiting and that the OCT imaging system 110 may be maintained by other entities and/or professionals that can use the OCT imaging system 110 to obtain OCT imaging data of retinas for the aforementioned or any other medical purposes.

In some embodiments, the health status identification system 101 may be maintained by an entity that is tasked with identifying or discovering biomarkers of tissue diseases or conditions from OCT images of the same. For example, the health status identification system 101 may be maintained by an ophthalmology healthcare provider, researcher, clinical trial administrator, etc., that is tasked with identifying or discovering biomarkers of retina diseases such as AMD. Although FIG. 1 shows the OCT imaging system 110 and the health status identification system 101 as two separate components, in some embodiments, the OCT imaging system 110 and the health status identification system 101 may be parts of the same system or module (e.g., and maintained by the same entity such as a health care provider or clinical trial administrator).

The health status identification system 101 may include an image processor 130 that is configured to receive OCT imaging data 112 from the OCT imaging system 110. The image processor 130 may be implemented using hardware, firmware, software, or a combination thereof. In one or more embodiments, the image processor 130 may be implemented within computing platform 102.

The image processor 130 may include model 132 (which may also be referred to as health status model 132), saliency mapping algorithm 134, and output generator 136. Model 132 may include a machine learning model. For example, model 132 may include a deep learning model. In one or more embodiments, the deep learning model includes a neural network model that comprises one or more neural networks. Model 132 can be used to identify (or classify) the current and/or future health status for the retina of a subject.

For example, model 132 may receive OCT imaging data 112 as input. In particular, model 132 may receive OCT volume image 114 of the retina of a subject. Model 132 may process OCT volume image 114 by processing at least a portion of the OCT slice images that make up OCT volume image 114. In some embodiments, model 132 processes every OCT slice image that makes up OCT volume image 114. Model 132 generates health indication output 138 based on OCT volume image 114 in which health indication output 138 indicates whether OCT volume image 114 evidences selected health status category 140 for the retina of the subject.

For example, the health indication output 138 may indicate a level of association between the OCT volume image 114 and selected health status category 140. This level of association may be indicated via a probability. For example, in one or more embodiments, the health indication output 138 may be a probability that indicates the level of association between the OCT volume image 114 and selected health status category 140 or how likely it is that the OCT volume image 114 evidences the selected health status category 140. This level of association may be, for example, no association (e.g., 0.0 probability), a weak association (e.g., between 0.01 and 0.4 probability), a moderate association (e.g., between 0.4 and 0.6 probability), a strong association (e.g., between 0.6 and 1.0 probability), or some other type of association. These percentages are merely some examples of probability ranges and levels of association. Other levels of association and/or other percentage ranges may be used in other embodiments. The process by which model 132 generates health indication output 138 is described in greater detail with respect to FIG. 2 below.

Selected health status category 140 may be a health status for the retina that refers to a current point in time or a future point in time (e.g., 6 months, 1 year, 2 years, etc. into the future). In other words, selected health status category 140 may represent a current health status or a future health status. The current point in time may be, for example, the time at which the OCT volume image 114 was generated within a selected interval (e.g., 1 week, 2 weeks, 1 month, 2 months, etc.) of the time at which the OCT volume image 114 was generated.

In one or more embodiments, selected health status category 140 may be a selected stage of AMD. Selected health status category 140 may be, for example, without limitation, current nascent GA or future nascent GA. In some instances, selected health status category 140 represents a stage of AMD that is predicted to lead to nascent GA within a selected period of time (e.g., 6 months, 1 year, 2, years, etc.). In other instances, selected health status category 140 represents a stage of AMD that is predicted to lead to the onset of GA within a selected period of time. In still other instances, selected health status category 140 represents a stage of AMD that is predicted to lead to nascent GA within a selected period of time. In this manner, selected health status category 140 may be for a current health status of the retina or a prediction of a future health status of the retina. Other examples of health status categories include, but are not limited to, early AMD, intermediate AMD, GA, etc.

As described above, model 132 may be implemented using a neural network model. The neural network model may include any number of or combination of neural networks. A neural network may take the form of, but is not limited to, a convolutional neural network (CNN) (e.g., a U-Net), a fully convolutional network (FCN) a stacked FCN, a stacked FCN with multi-channel learning, a feed-forward neural network (FNN), a recurrent neural network (RNN), a modular neural network (MNN), a residual neural network (ResNet), an ordinary differential equations neural network (neural-ODE), a Squeeze and Excitation embedded neural network, a MobileNet, or another type of neural network. In one or more embodiments, a neural network may itself be comprised of at least one of a CNN (e.g., a U-Net), a FCN, a stacked FCN, a stacked FCN with multi-channel learning, a FNN, a RNN, an MNN, a ResNet, a neural-ODE, a Squeeze and Excitation embedded neural network, a MobileNet, or another type of neural network. In one or more embodiments, the neural network model takes the form of a convolutional neural network (CNN) system that includes one or more convolutional neural networks. For example, the CNN may include a plurality of neural networks, each of which may itself be a convolutional neural network.

In one or more embodiments, the neural network model may include a set of encoders, each of which can be a single encoder or multiple encoders, and a decoder. In some embodiments, the one or more encoders and/or the decoder may be implemented via a neural network, which may, in turn, be comprised of one or more neural networks. In some instances, the decoder and the one or more encoders may be implemented using a CNN. The decoder and the one or more encoders may also be implemented as a Y-Net (Y-shaped neural network system) or a U-Net (U-shaped neural network system). Further details related to neural network are provided below with reference to FIG. 6.

The health status identification system 101 may also be used to identify (or detect) a set of biomarkers 142 for selected health status category 140. For example, the health status identification system 101 may be used to identify set of biomarkers 142 in the OCT volume image 114 that evidence selected health status category 140 for the retina of the subject. For example, when selected health status category 140 is current nascent GA, set of biomarkers 142 may include one or more anatomic biomarkers that indicate that the OCT volume image 114 currently evidences selected health status category 140 for the retina. When selected health status category 140 represents future health status (e.g., predicted to progress to nascent GA within a selected period of time), set of biomarkers 142 may be prognostic for this future health status.

The health status identification system 101 uses saliency mapping algorithm 134 to identify set of biomarkers 142. For example, saliency mapping algorithm 134 may be used to identify the portions (or regions) of the OCT volume image 114 that most impacted or contributed the most to the health indication output 138 of model 132. For example, saliency mapping algorithm 134 may indicate the degree of importance for the various portions (or regions) of the OCT volume image 114 for selected health status category 140.

Saliency mapping algorithm 134 may include, but is not limited to, Grad-CAM, CAM, SmoothGrad, VarGrad, another type of saliency mapping algorithm or technique, or a combination thereof. The saliency mapping algorithm 134 may generate saliency volume map 144, which indicates (e.g., via a heatmap) the degree of importance for the various portions (or regions) of the OCT volume image 114 with respect to selected health status category 140. In other words, saliency volume map 144 indicates the level of contribution of the various portions of the OCT volume image 114 to the health indication output 138 generated by the model 132. Saliency volume map 144 may be comprised of a plurality of saliency maps, each of which corresponds to a different one of the plurality of OCT slice images in the OCT volume image 114. Each saliency map may visually indicate (e.g., via color, highlighting, shading, pattern, outlining, text, annotations, etc.) the regions of the corresponding OCT slice image that were most impactful to model 132 for selected health status category 140.

Output generator 136 may receive and process saliency volume map 144 to generate map output 146. In one or more embodiments, map output 146 takes the form of a filtered or modified form of saliency volume map 144. In other embodiments, map output 146 takes the form of saliency volume map 144 or a modified form of saliency volume map 144 overlaid on OCT volume image 114. Similar to how saliency volume map 144 may be comprised of multiple saliency maps (two-dimensional), map output 146 may be comprised of multiple individual two-dimensional maps. These maps may be heat maps or overlays of heat maps over OCT slice images.

In one or more embodiments, a filter (e.g., threshold filter) may be applied to saliency volume map 144 to identify a subset of the saliency maps in saliency volume map 144 to be modified. The threshold filter may be set to ensure that only those saliency maps indicating a contribution of, for example, at least one region in the corresponding OCT slice image above a selected threshold are selected for the subset. This subset of saliency maps may then be modified such that the modified saliency volume map that is formed includes fewer maps than the saliency volume map 144. In this manner, when map output 146 is generated, map output 146 may be comprised of fewer maps than saliency volume map 144. In other embodiments, other types of filtering steps and/or other preprocessing steps may be performed such that map output 146 that is generated includes a fewer number of maps than the maps in saliency volume map 144.

Map output 146 may indicate whether a set of regions in OCT volume image 114 is associated with the selected health status category. For example, map output 146 may indicate a level of contribution of a set of regions in OCT volume image 114 to the health indication output 138 generated by the model 132. A region may be a pixel-level region or a region formed by multiple pixels. A region may be a continuous or discontinuous region. In some embodiments, map output 146 visually localizes set of biomarkers 142. In other embodiments, map output 146 may be further processed by output generator 136 to identify which of the regions of OCT volume image 114 are or include biomarkers. The process of identifying set of biomarkers 142 using saliency mapping algorithm 134 and output generator 136 is described in greater detail with respect to FIGS. 2-3 below. In some embodiments, saliency mapping algorithm 134 is integrated with or implemented as part of output generator 136.

In some embodiments, the model 132 may be trained with training dataset 148, which may include OCT volume images of tissues, so that the model 132 is capable of identifying and/or discovering biomarkers associated with a health status category of the tissues (e.g., diseases, conditions, disease progressions, etc.,) from a test dataset of OCT volume images of said tissues. In some instances, the health status category of a tissue may range from healthy to the various stages of a disease. For example, the health status categories associated with a retina can range from healthy to the various stages of AMD, including but not limited to early AMD, intermediate AMD, nascent GA, etc. In some instances, different biomarkers may be associated with the different health status categories of a disease.

For example, AMD is a leading cause of vision loss in patients 50 years or older Initially, AMD manifests as a dry type of AMD before progressing to a wet type at a later stage. For the dry type, small deposits, called drusen, form beneath the basement membrane of the retinal pigment epithelium (RPE) and the inner collagenous layer of the Bruch's membrane (BM) of the retina, causing the retina to deteriorate in time. In its advanced stage, dry AMD can appear as geographic atrophy (GA), which is characterized by progressive and irreversible loss of choriocapillaries, RPE, and photoreceptors. Wet type AMD manifests with abnormal blood vessels originating in the choroid layer of the eye growing into the retina and leaking fluid from the blood into the retina. As such, in some embodiments, drusen may be considered biomarkers of one type of health status category of AMD (e.g., the dry type of AMD), while a missing RPE may be considered a biomarker of another type of health status category of AMD (e.g., the wet type of AMD). It is to be noted that other health status categories (e.g., intermediate AMD, nascent GA, etc.) may be defined for AMD (e.g., or other types of retinal diseases) and that at least one or more differentiable biomarkers may be associated with these health status categories.

As noted above, morphological changes to, and/or the appearance of new, regions, boundaries, etc., in a retina or an eye may be considered as biomarkers of the retinal diseases such as AMD. Examples of such morphological changes may include distortions (e.g., shape, size, etc.), attenuations, abnormalities, missing or absent regions/boundaries, defects, lesions, and/or the like. For instance, as mentioned above, a missing RPE may be indicative of a retinal degenerative disease such as AMD. As another example, the appearance of regions, boundaries therebetween, etc., that are not present in a healthy eye or retina, such as deposits (e.g., drusen), leaks, etc., may also be considered as biomarkers of retinal diseases such as AMD. Other examples of features in a retina that may be considered as biomarkers include a reticular pseudodrusen (RPD), a retinal hyperreflective foci (e.g., a lesion with equal or greater reflectivity than the RPE), a hyporeflective wedge-shaped structure (e.g., appearing within the boundaries of the OPL), choroidal hypertransmission defects, and/or the like.

Output generator 136 may generate other forms of output. For example, in one or more embodiments, output generator may generate a report 150 to be displayed on display system 106 or to be sent over network 120 or another network to a remote device (e.g., cloud, mobile device, laptop, tablet, etc.). The report 150 may include, for example, without limitation, the OCT volume image 114, the saliency volume image, the map output for the OCT volume image, a list of any identified biomarkers, a treatment recommendation for the retina of the subject, an evaluation recommendation, a monitoring recommendation, some other type of recommendation or instruction, or a combination thereof. The monitoring recommendation may, for example, include a plan for monitoring the retina of the subject and a schedule for future OCT imaging appointments. The evaluation recommendation may include, for example, a recommendation to further review (e.g., manually review by a human reviewer) a subset of the plurality of OCT slice images that form the OCT volume image. The subset identified may include fewer than 5% of the plurality of OCT slice images. In some cases, the subset may include fewer than 50%, 45%, 40%, 35%, 30%, 25%, 20%, 15%, 10%, 5%, 2%, or some other percentage of the plurality of OCT slice images.

In one or more embodiments, the health status identification system 101 stores the OCT volume image 114 obtained from the OCT imaging system 110, saliency map 144, map output 146, an identification of the set of biomarkers 142, report 150, other data generated during the processing of the OCT volume image 114, or a combination thereof in data structure 104. In some embodiments, the portion of data structure 104 storing such information may be configured to comply with the security requirements of the Health Insurance Portability and Accountability Act (HIPAA) that mandate certain security procedures when handling patient data (e.g., such as OCT images of tissues of patients), i.e., the data structure 104 may be HIPAA-compliant. For instance, the information being stored may be encrypted and anonymized. For example, the OCT volume image 114 may be encrypted as well as processed to remove and/or obfuscate personally identifying information (PII) of the subjects from which the OCT volume image 114 was obtained. In some instances, the communications link between the OCT imaging system 110 and the health status identification system 101 that utilizes the network 120 may also be HIPAA-compliant. For example, the communication links may be a virtual private network (VPN) that is end-to-end encrypted and configured to anonymize PII data transmitted therein.

In one or more embodiments, the health identification system 101 includes a system interface 160 that enables human reviewers to interact with the images, maps, and/or other outputs generated by the health identification system 101. The system interface 160 may include, for example, but is not limited to, a web browser, an application interface, a web-based user interface, some other type of interface component, or a combination thereof.

Although the discussion herein is generally directed to the classification of OCT volume images (and OCT slice images) with respect to stages of AMD and the identification and discovery of biomarkers of AMD from OCT volume images (or OCT slice images) of retinas, the discussion may equally apply to medical images of other tissues of a subject obtained using any other medical imaging technology. That is, the OCT volume image 114 and the related discussion about the steps for classifying the OCT volume image 114 and for the identification and/or discovery of AMD biomarkers via the generation of saliency maps (e.g., heatmaps) of the retinal OCT slice images are intended as non-limiting illustrations, and same or substantially similar method steps may apply for the identification and/or discovery of other tissue diseases from 3D images (e.g., OCT or otherwise) of the tissues.

III. Exemplary Methodologies for Identifying Health Status

III.A. Exemplary Health Status Classification and Biomarker Identification

Figure 2:
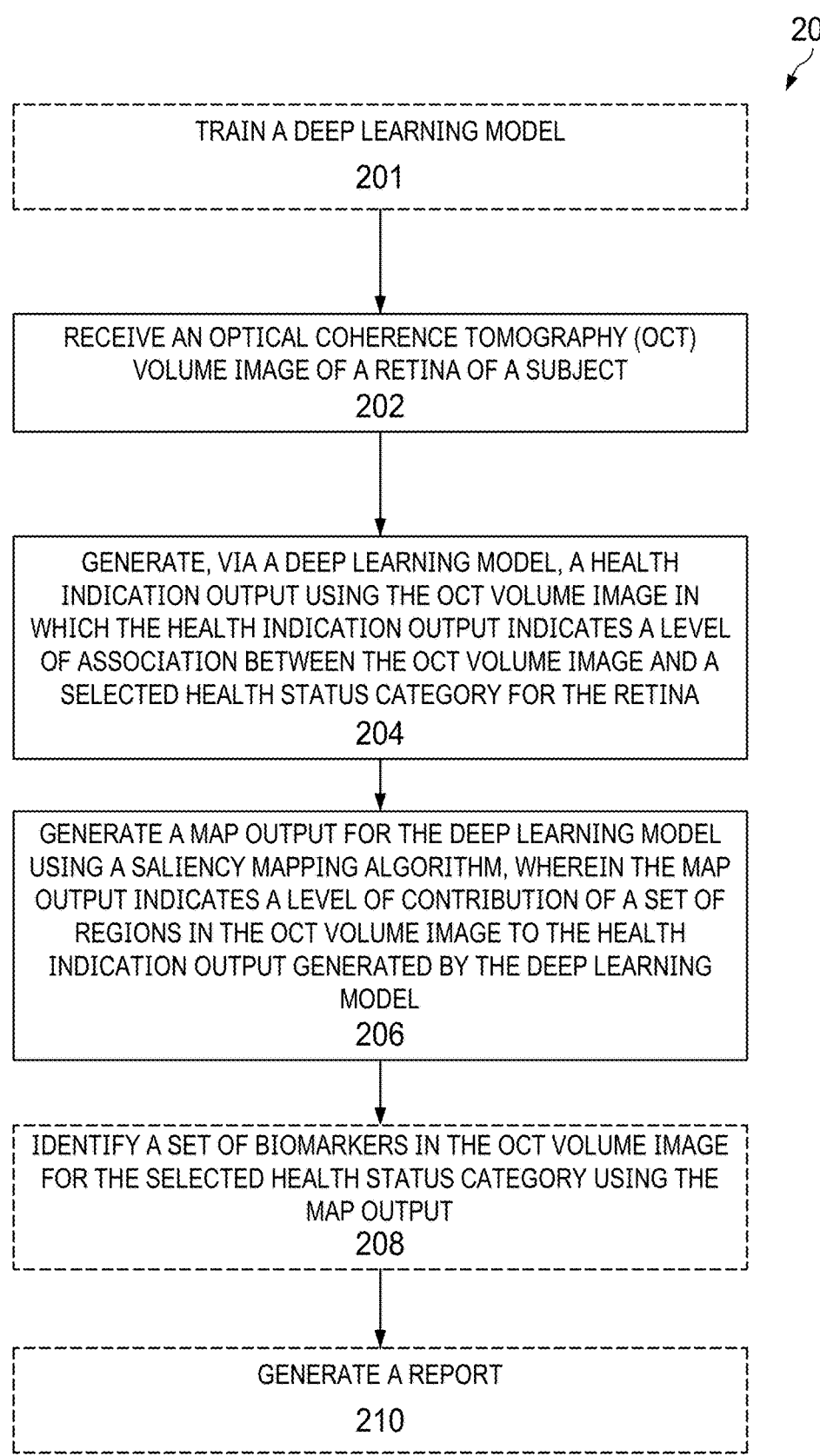
FIG. 2 is a flowchart of a process for processing an OCT volume image of a retina of a subject to determine whether the OCT volume image evidences a selected health status category for the retina in accordance with various embodiments.

FIG. 2 is a flowchart of a process for processing an OCT volume image of a retina of a subject to determine whether the OCT volume image evidences a selected health status category for the retina in accordance with various embodiments. Process 200 in FIG. 2 may be implemented using health status identification system 101 in FIG. 1. For example, at least some of the steps of the process 200 may be performed by the processors of a computer or a server implemented as part of health status identification system 101. Process 200 may be implemented using model 132, saliency mapping algorithm 134, and/or output generator 136 in FIG. 1. Further, it is understood that additional steps may be performed before, during, or after the steps of process 200 discussed below. In addition, in some embodiments, one or more of the steps may also be omitted or performed in different orders.

Process 200 may optionally include the step 201 of training a deep learning model. The deep learning model may be one example of an implementation for model 132 in FIG. 1. The deep learning model may include, for example, without limitation, a neural network model. The deep learning model may be trained on a training dataset such as, for example, without limitation, training dataset 148 in FIG. 1. Examples of how the deep learning model may be trained are described in further detail below in Section III.B.

Step 202 of process 200 includes receiving an optical coherence tomography (OCT) volume image of a retina of a subject. The OCT volume image may be, for example, OCT volume image 114 in FIG. 1. The OCT volume image may be comprised of a plurality of OCT slice images.

Step 204 includes generating, via a deep learning model, a health indication output using the OCT volume image in which the health indication output indicates a level of association between the OCT volume image and a selected health status category for the retina. The health indication output may be, for example, health indication output 138 in FIG. 1. In one or more embodiments, the health indication output is a classification score. The classification score may be, for example, a probability that the OCT volume image, and thereby the retina captured in the OCT volume image, can be classified as being of the selected health status category. In other words, the classification score may be the probability that the OCT volume images evidences the selected health status category for the retina. In some embodiments, a threshold for the probability score (e.g., >0.5, >0.6, >0.7, >0.75, >0.8, etc.) is used to determine whether the OCT volume image evidences the selected health status category or not.

The selected health status category may be, for example, selected health status category 140 in FIG. 1. In one or more embodiments, the selected health status category represents a current health status for the retina (e.g., a current disease state). In one or more other embodiments, the selected health status category represents a future health status (e.g., a future disease state that is predicted to develop within a selected period of time). For example, the selected health status category may represent nascent GA that is either currently present or predicted to develop within a selected period of time (e.g., 3 months, 6 months, 1 year, 2 years, 3 years, or some other period of time).

The deep learning model may generate the health indication output in different ways. In one or more embodiments, the deep learning model generates an initial output for each OCT slice image in the OCT volume image to form a plurality of initial outputs. The initial output for an OCT slice image may be, for example, without limitation, a probability that the OCT slice image evidences the selected health status category for the retina. The deep learning model may use the plurality of initial outputs to generate the health indication output. For example, the deep learning model may average the plurality of initial outputs together to generate a health indication output that is a probability that the OCT volume image as a whole evidences the selected health status category for the retina. In other words, the health indication output may be a probability that the retina can be classified with the selected health status category. In other embodiments, the median of the plurality of initial outputs may be used as the health indication output. In still other embodiments, the plurality of initial outputs may be combined or integrated in some other manner to generate the health indication output.

Step 206 includes generating a map output (e.g., map output 146) for the deep learning model using a saliency mapping algorithm, wherein the map output indicates a level of contribution of a set of regions in the OCT volume image to the health indication output generated by the deep learning model. The level of contribution of a region in the OCT volume may be the degree of importance or impact that the region has on the health indication output generated by the deep learning model. This region may be defined as a single pixel or multiple pixels. The region may continuous or discontinuous. In one or more embodiments, the saliency mapping algorithm receives data from the deep learning model. This data may include, for example, features, weights, or gradients used by the deep learning model to generate the health indication output in step 204. The saliency map algorithm may be used to generate a saliency map (or heatmap) that indicates a degree of importance for the various portions of the OCT volume image with respect to the selected health status category (which is the class of interest).

For example, the saliency mapping algorithm may generate a saliency map for each OCT slice image of the OCT volume image. In one or more embodiments, the saliency mapping algorithm is implemented using Grad-CAM. The saliency map may be, for example, a heatmap that indicates the level of contribution (or degree of importance) of each pixel in the corresponding OCT slice image to the health indication output generated by the deep learning model with respect to the selected health status category. The saliency maps together for the plurality of OCT slice images in the OCT volume image may form a saliency volume map. The saliency maps may use color, annotations, text, highlighting, shading, patterns, or some other type of visual indicator to indicate degree of importance. In one example, a range of colors may be used to indicate a range of degrees of importance.

The saliency volume map may be used to generate the map output in various ways. In one or more embodiments, each saliency map for each OCT slice image may be filtered to generate a modified saliency map. For example, one or more filters (e.g., threshold, processing filters, numerical filters, color filters, shading filters, etc.) may be applied to the saliency maps to generate modified saliency maps that together form a modified saliency volume map. Each modified saliency map may visually signal the most important regions of the corresponding OCT slice image. In one or more embodiments, each modified saliency map is overlaid over its corresponding OCT slice image to generate the map output. For example, a modified saliency map may be overlaid over the corresponding OCT slice image such that the portion(s) of the OCT slice image determined to be most important (or relevant) to the model for the selected health status category is indicated. In one or more embodiments, the map output includes all of the overlaid OCT slice images. In one or more embodiments, the map output may provide a visual indication on each overlaid OCT slice image of the regions having the most important or impactful contribution to the generation of the health indication output.

In other embodiments, the modified saliency maps are processed in another manner to generate a map output that indicates which regions of the OCT slice images are most impactful to the model for the selected health status category. For example, information from the modified saliency maps may be used to annotate and/or otherwise graphically modify the corresponding OCT slice images to form the map output.

Process 200 may optionally include step 208. Step 208 includes identifying a set of biomarkers (e.g., set of biomarkers 142 in FIG. 1) in the OCT volume image for the selected health status category using the map output. Step 208 may be performed in different ways. In one or more embodiments, a potential biomarker region may be identified in association with a selected region of an OCT slice image identified by the map output as being important or impactful to the selected health status category. The potential biomarker region may be identified as this selected region of the OCT slice image or may be defined based on this selected region of OCT slice image. In one or more embodiments, a bounding box is created around the selected region of the OCT slice image to define the potential biomarker region.

A scoring metric may be generated for the potential biomarker region. The scoring metric may include, for example, a size of the potential biomarker region, a confidence score for the potential biomarker region, some other metric, or a combination thereof. The potential biomarker region (e.g., bounding box) may be identified as a biomarker for the selected health status category when the scoring metric meets a selected threshold. For example, if the scoring metric includes a confidence score and dimensions, then the selected threshold may include a confidence score threshold (e.g., score minimum) and minimum dimensions. In some embodiments, a particular biomarker may be found on or span multiple OCT slice images. In one or more embodiments, the bounding boxes that meet the threshold and that are classified as biomarker regions may be identified on the corresponding OCT slice images to form biomarker maps.

One or more of the biomarkers that are identified may be known biomarkers that have been previously seen by human reviewers. In some embodiments, one or more of the biomarkers may be new, not previously known biomarkers. In other words, the identification of the set of biomarkers in step 208 may include the discovery of one or more new biomarkers associated with the selected health status category. The discovery of one or more new biomarkers may be more prone to occur, for example, when the selected health status category represents a future health status that is predicted to develop (e.g., a future progression of AMD from early AMD or intermediate AMD to nascent GA; from nascent GA to GA; from intermediate AMD to GA, etc.).

Process 200 may optionally include step 210. Step 210 includes generating a report. The report may include, for example, without limitation, the OCT volume image, the saliency volume image, the map output for the OCT volume image, a list of any identified biomarkers, a treatment recommendation for the retina of the subject, an evaluation recommendation, a monitoring recommendation, some other type of recommendation or instruction, or a combination thereof. The monitoring recommendation may, for example, include a plan for monitoring the retina of the subject and a schedule for future OCT imaging appointments. The evaluation recommendation may include, for example, a recommendation to further review (e.g., manually review by a human reviewer) a subset of the plurality of OCT slice images that form the OCT volume image. The subset identified may include fewer than 5% of the plurality of OCT slice images. In some cases, the subset may include fewer than 50%, 45%, 40%, 35%, 30%, 25%, 20%, 15%, 10%, 5%, 2%, or some other percentage of the plurality of OCT slice images.

In some embodiments, the health identification system 101 in FIG. 1 may prompt (e.g., via an evaluation recommendation in report 150 in FIG. 1) user review of a particular subset of the OCT slice images within the OCT volume image to identify one or more features (or biomarkers) in the same or substantially similar locations as the bounding boxes identified on biomarker maps. For example, in some cases, the health identification system 101 may include a system interface 160 that allows reviewers (e.g., healthcare professionals, trained reviewers, etc.) to access, review and annotate the OCT slice images of the OCT volume image so as to identify and/or discover biomarkers. That is, for example, the system interface 160 may facilitate the annotation, by the reviewers, of the OCT slice images with biomarkers. In some instances, instead of or in addition to allowing reviewers to identify biomarkers on the OCT slice images shown in the biomarker maps, the system interface 160 may be configured to allow reviewers to correct or adjust the bounding boxes (e.g., adjust the size, shape, or continuity of the bounding boxes) on the biomarker maps. In some cases, the reviewers can annotate the bounding boxes to indicate the adjustments to be made. In some cases, the annotated and/or adjusted biomarker maps created by the reviewers may be fed back to the deep learning model (e.g., as part of the training dataset 148) for additional training of the deep learning model.

FIG. 3 is a flowchart of a process for identifying biomarkers in an OCT volume image of a retina of a subject in accordance with various embodiments. Process 300 in FIG. 3 may be implemented using health status identification system 101 in FIG. 1. For example, at least some of the steps of the process 300 may be performed by the processors of a computer or a server implemented as part of health status identification system 101. Process 300 may be implemented using model 132, saliency mapping algorithm 134, and/or output generator 136 in FIG. 1. Further, it is understood that additional steps may be performed before, during, or after the steps of process 200 discussed below. In addition, in some embodiments, one or more of the steps may also be omitted or performed in different orders.

Process 300 may optionally include the step 302 of training a deep learning model. The deep learning model may be one example of an implementation for model 132 in FIG. 1. The deep learning model may include, for example, without limitation, a neural network model. The deep learning model may be trained on a training dataset such as, for example, without limitation, training dataset 148 in FIG. 1. Examples of how the deep learning model may be trained are described in further detail below in Section III.B.

Step 304 of process 300 includes receiving an optical coherence tomography (OCT) volume image of a retina of a subject. The OCT volume image may be, for example, OCT volume image 114 in FIG. 1. The OCT volume image may be comprised of a plurality of OCT slice images.

Step 306 of process 300 includes generating, via a deep learning model, a health indication output using the OCT volume image in which the health indication output indicates a level of association between the OCT volume image and a selected health status category for the retina. For example, the health indication output may be a probability that indicates how likely the classification of the retina in the OCT volume image is the selected health status category. In other words, the health indication output may be probability that indicates how likely it is that the OCT volume image evidences the selected health status category for the retina.

Step 308 of process 300 includes generating a saliency volume map for the OCT volume image using a saliency mapping algorithm, wherein the saliency volume map indicates a level of contribution of a set of regions in the OCT volume image to the health indication output generated by the deep learning model. Step 308 may be performed in a manner similar to the generation of the saliency volume map described with respect to step 206 in FIG. 2. The saliency mapping algorithm may include, for example, a Grad-CAM algorithm. The level of contribution may be determined based on the features, gradients, or weights used in the deep learning model (e.g., the features, gradients, or weights used in the last activation layer of the deep learning model).

Step 310 of process 300 includes detecting a set of biomarkers for a selected health status category using the saliency volume map. Step 310 may be implemented in a manner similar to the identification of biomarkers described above with respect to step 208 in FIG. 2. For example, step 310 may include filtering the saliency volume map to generate a modified saliency volume map. The modified saliency volume map identifies a set of regions that are associated with the selected health status category. Step 310 may further include identifying a potential biomarker region in association with a region of the set of regions. A scoring metric may be generated for the potential biomarker region. The potential biomarker region may be identified as including at least one biomarker when the scoring metric meets a selected threshold.

III.B. Exemplary Training of Deep Learning Model

The deep learning model described above in FIG. 1 (e.g., model 132), FIG. 2, and FIG. 3 may be trained in different ways. In one or more embodiments, the deep learning model is trained with a training dataset (e.g., training dataset 148 in FIG. 1) that includes one or more training OCT volume images. Each of these training OCT volume images may be of a different retina that has been identified as displaying a disease or a condition corresponding to the selected health status category (e.g., nascent GA, etc.). The retinas may have been displaying the disease or condition for a length of time at least substantially equal to the duration after the training OCT volume image is taken or generated.

In one or more embodiments, the deep learning model (e.g., model 132 in FIG. 1, the deep learning model described in FIGS. 2-3) may be trained to classify the health status of a retina based on a training dataset (e.g., training dataset 148 in FIG. 1) of OCT volume images of retinas of patients suffering from one or more health status categories so that the deep learning model may learn what features of the retina, and locations thereof, in the OCT volume images are signals for the one or more health status categories. When provided with a test dataset of OCT volume images, the trained deep learning model may then be able to efficiently and accurately identify whether the OCT volume images evidence a selected health status category.

A training dataset of OCT volume images may include OCT images of retinas of patients that are known to be suffering from a given stage of AMD (i.e., the health status category of the retinas may be the said stage of AMD). In such cases, the deep learning model may be trained with the training dataset to learn what features in the OCT volume images correspond to, are associated with, or signal that stage of AMD. For example, the patients may be sufferers of late-stage AMD, and the deep learning model may identify, or discover, from the training dataset of OCT volume images of the patients' retinas that the anatomical features in an OCT volume image representing a severely deformed RPE may be evidence of late-stage AMD. In such cases, when provided with an OCT volume image of a retina of a patient showing a severely deformed RPE, the trained deep learning model may identify the OCT volume image as one that belongs to a late-stage AMD patient.

In some embodiments, the deep learning model may be capable of classifying health status even based on unknown biomarkers of retinal diseases. For example, the deep learning model may be provided with a training dataset of OCT volume images of retinas of patients that are suffering from some retinal disease (e.g., nascent GA) all the biomarkers of which may not be known. That is, the biomarkers for that selected health status category (e.g., nascent GA) of the retinal disease may not be known. In such cases, the deep learning model may process the dataset of OCT volume images and learn that a feature or a pattern in the OCT volume images, e.g., lesions, is evidence of the selected health status category.

IV. Exemplary OCT Images and Saliency Maps

Figure 4:
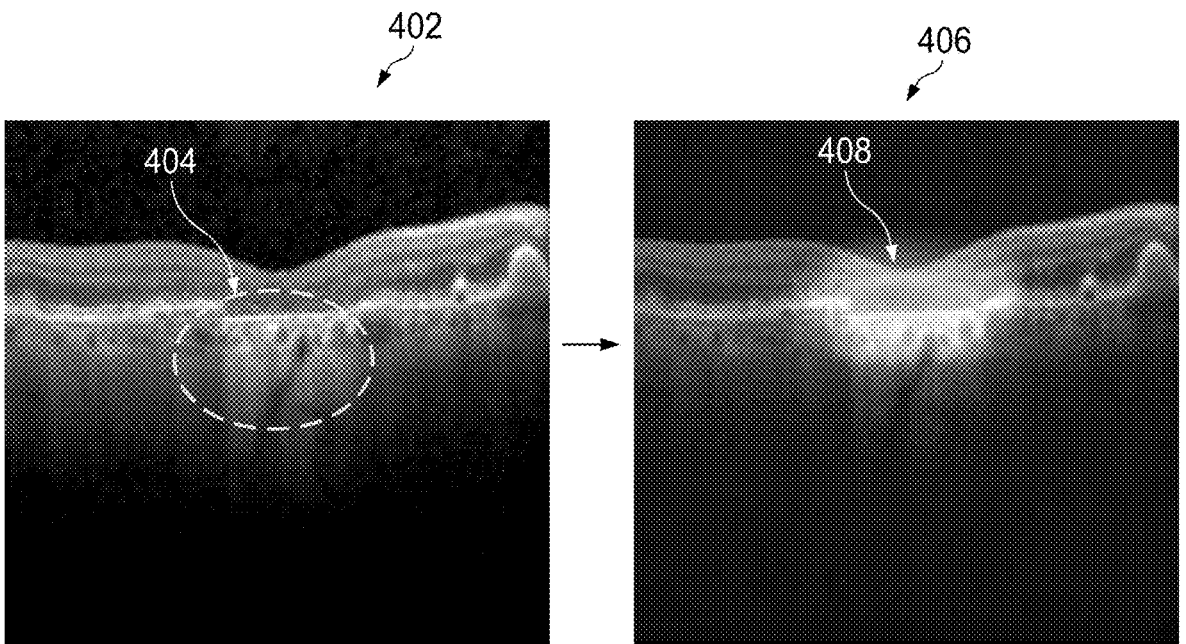
FIG. 4 illustrates an annotated OCT slice image and a corresponding heatmap for the annotated OCT slice image in accordance with various embodiments.

FIG. 4 illustrates an annotated OCT slice image and a corresponding heatmap for the annotated OCT slice image in accordance with various embodiments. The OCT slice image 402 may be one example of an implementation for an OCT slice image in OCT volume image 114 in FIG. 1. The OCT slice image 402 may also be one example of an implementation from an OCT slice image in training dataset 148 in FIG. 1. OCT slice image 402 includes annotated region 404 that has been marked by a human grader as being a biomarker for nascent GA.

Heatmap 406 is one example of an implementation for at least a portion of map output 146 in FIG. 1. Heatmap 406 may be the result of overlaying a saliency map generated using a saliency mapping algorithm such as saliency mapping algorithm 134 in FIG. 1 (e.g., generated using Grad-CAM) over OCT slice image 402. The saliency map was generated for a trained deep learning model that processed OCT slice image 402. Heatmap 406 indicates that region 408 was most impactful to the model for nascent GA and shows that the deep learning model, which may be, for example, model 132 in FIG. 1, accurately used the correct region of the OCT slice image 402 for its classification with respect to nascent GA.

Heatmap 406 may be used to identify and localize the biomarker shown within region 408 for nascent GA. For example, an output may be generated that identifies an anatomic biomarker located within region 408. The biomarker may be, for example, a lesion in the retina, missing retinal pigment epithelium (RPE), a detached layer of the retina, or some other type of biomarker. In some cases, more than one biomarker may be present within region 408. In some instances, filtering may be performed to identify certain pixels within region 408 of heatmap 406 or within region 404 of the OCT slice image 402 that are a biomarker. In some instances, the size of region 408 may be used to determine whether region 408 contains one or more biomarkers. In one or more embodiments, the size of region 408 is greater than about 20 pixels.

Such identification and localization of biomarkers may allow a healthcare practitioner to diagnose, monitor, treat, etc., the patient whose retina is depicted in the OCT slice image 402. For example, an ophthalmologist reviewing the heatmap 406 or information generated based on the heatmap 406 may be able to recommend a treatment option or monitoring option prior to the onset of GA.

Figure 5:
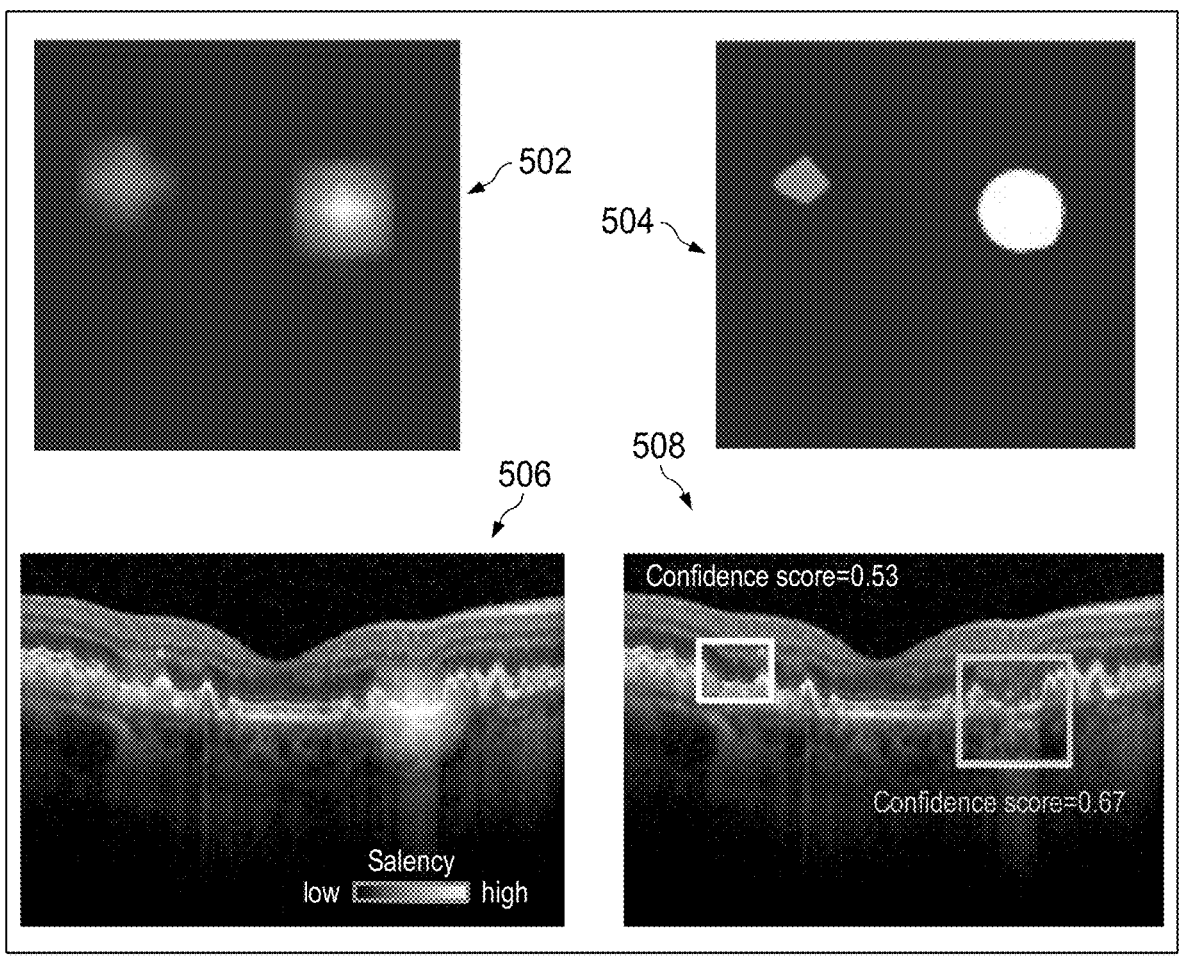
FIG. 5 is an illustration of different maps in accordance with various embodiments.

FIG. 5 is an illustration of different maps in accordance with various embodiments. Saliency map 502 is one example of an implementation for a saliency map that makes up saliency volume map 144 in FIG. 1. Modified saliency map 504 is one example of an implementation for a saliency map that has been modified after filtering (e.g., applying a threshold filter). Heatmap 506 is one example of an implementation for a component of map output 146 in FIG. 1. Heatmap 506 includes a modified overlay of saliency map 502 over an OCT slice image.

Biomarker map 508 is an example of an implementation for an output that may be generated by output generator 136 in FIG. 1 using heatmap 506. In biomarker map 508, a first bounding box identifies a potential biomarker region that does not have a sufficiently high confidence score (e.g., >0.6) to be considered a biomarker region that includes at least one biomarker. Further, biomarker map 508 includes a second bounding box that identifies a potential biomarker region that has a sufficiently high confidence score to be considered a biomarker region that includes at least one biomarker.

V. Exemplary Neural Network

Figure 6:
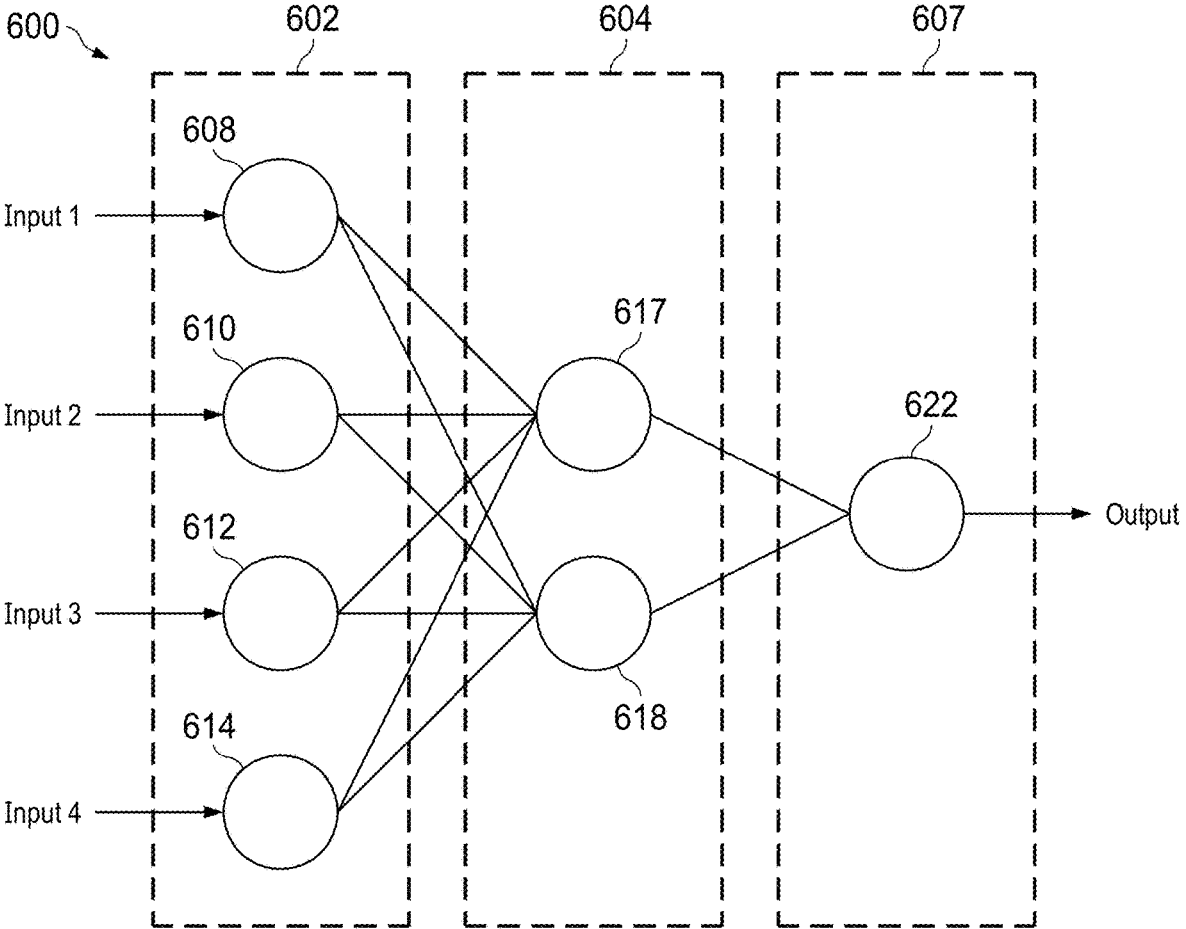
FIG. 6 illustrates an example neural network that can be used to implement a computer-based model according to various embodiments of the present disclosure.

FIG. 6 illustrates an example neural network that can be used to implement a computer-based model according to various embodiments of the present disclosure. For example, the neural network 600 may be used to implement the model 132 of the health status identification system 101. As shown, the artificial neural network 600 includes three layers—an input layer 602, a hidden layer 604, and an output layer 607. Each of the layers 602, 604, and 607 may include one or more nodes. For example, the input layer 602 includes nodes 608-614, the hidden layer 604 includes nodes 617 and 618, and the output layer 607 includes a node 622. In this example, each node in a layer is connected to every node in an adjacent layer. For example, the node 608 in the input layer 602 is connected to both of nodes 617 and 618 in the hidden layer 604. Similarly, the node 617 in the hidden layer 604 is connected to all of the nodes 608-614 in the input layer 602 and the node 622 in the output layer 607. Although only one hidden layer is shown for the artificial neural network 600, it has been contemplated that the artificial neural network 600 used to implement the model 132 may include as many hidden layers as necessary or desired.

In this example, the artificial neural network 600 receives a set of input values and produces an output value. Each node in the input layer 602 may correspond to a distinct input value. For example, when the artificial neural network 600 is used to implement the model 132, each node in the input layer 602 may correspond to a distinct attribute of an OCT volume image of a retina (e.g., obtained from the OCT imaging system 110).

In some embodiments, each of the nodes 617 and 618 in the hidden layer 604 generates a representation, which may include a mathematical computation (or algorithm) that produces a value based on the input values received from the nodes 608-614. The mathematical computation may include assigning different weights to each of the data values received from the nodes 608-614. The nodes 617 and 618 may include different algorithms and/or different weights assigned to the data variables from the nodes 608-614 such that each of the nodes 617 and 618 may produce a different value based on the same input values received from the nodes 608-614. In some embodiments, the weights that are initially assigned to the features (or input values) for each of the nodes 617 and 618 may be randomly generated (e.g., using a computer randomizer). The values generated by the nodes 617 and 618 may be used by the node 622 in the output layer 607 to produce an output value for the artificial neural network 600. When the artificial neural network 600 is used to implement the model 132, the output value produced by the artificial neural network 600 may include a saliency map such as but not limited to a heatmap of the OCT volume image of a retina (e.g., saliency map 144) identifying biomarkers therein.

The artificial neural network 600 may be trained by using training data. For example, the training data herein may be OCT volume images of retinas. By providing training data to the artificial neural network 600, the nodes 617 and 618 in the hidden layer 604 may be trained (adjusted) such that an optimal output is produced in the output layer 607 based on the training data. By continuously providing different sets of training data, and penalizing the artificial neural network 600 when the output of the artificial neural network 600 is incorrect (e.g., when incorrectly identifying a biomarker in the OCT volume images), the artificial neural network 600 (and specifically, the representations of the nodes in the hidden layer 604) may be trained (adjusted) to improve its performance in data classification. Adjusting the artificial neural network 600 may include adjusting the weights associated with each node in the hidden layer 604.

Although the above discussions pertain to an artificial neural network as an example of machine learning, it is understood that other types of machine learning methods may also be suitable to implement the various aspects of the present disclosure. For example, support vector machines (SVMs) may be used to implement machine learning. SVMs are a set of related supervised learning methods used for classification and regression. A SVM training algorithm—which may be a non-probabilistic binary linear classifier—may build a model that predicts whether a new example falls into one category or another. As another example, Bayesian networks may be used to implement machine learning. A Bayesian network is an acyclic probabilistic graphical model that represents a set of random variables and their conditional independence with a directed acyclic graph (DAG). The Bayesian network could present the probabilistic relationship between one variable and another variable. Another example is a machine learning engine that employs a decision tree learning model to conduct the machine learning process. In some instances, decision tree learning models may include classification tree models, as well as regression tree models. In some embodiments, the machine learning engine employs a Gradient Boosting Machine (GBM) model (e.g., XGBoost) as a regression tree model. Other machine learning techniques may be used to implement the machine learning engine, for example via Random Forest or Deep Neural Networks. Other types of machine learning algorithms are not discussed in detail herein for reasons of simplicity and it is understood that the present disclosure is not limited to a particular type of machine learning.

VI. Computer Implemented System

Figure 7:
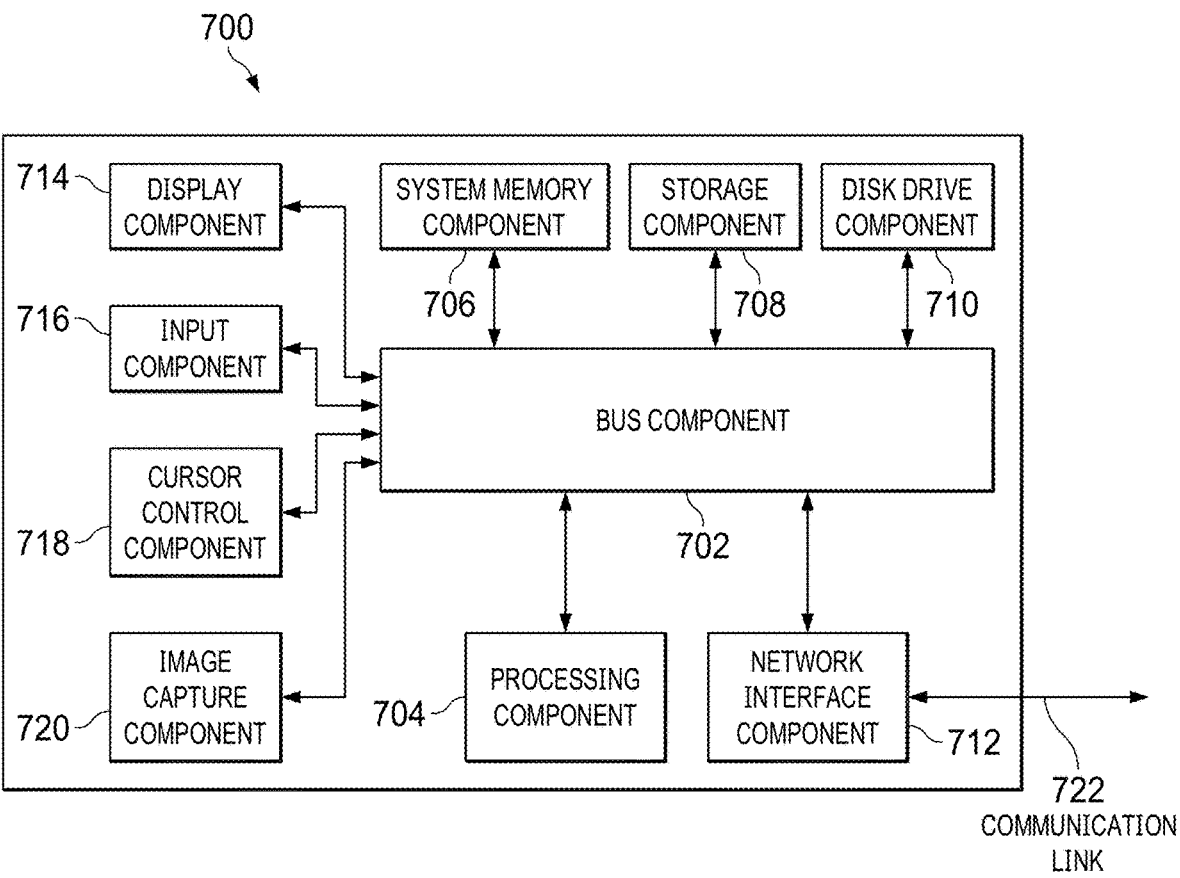
FIG. 7 is a block diagram of a computer system in accordance with various embodiments of the present disclosure.

FIG. 7 is a block diagram of a computer system 700 suitable for implementing various methods and devices described herein, for example, the OCT imaging system 110, the health status identification system 101, and/or the like. In various implementations, the devices capable of performing the steps may comprise imaging systems (e.g., OCT scanner or imaging system, etc.), a network communications device (e.g., mobile cellular phone, laptop, personal computer, tablet, workstation, etc.), a network computing device (e.g., a network server, a computer processor, an electronic communications interface, etc.), or another suitable device. Accordingly, it should be appreciated that the devices capable of implementing the aforementioned servers and modules, and the various method steps of the process 200 in FIG. 2 and process 300 in FIG. 3 discussed above, may be implemented as the computer system 700 in a manner as follows.

In accordance with various embodiments of the present disclosure, the computer system 700, such as a network server, a workstation, a computing device, a communications device, etc., includes a bus component 702 or other communication mechanisms for communicating information, which interconnects subsystems and components, such as a computer processing component 704 (e.g., processor, micro-controller, digital signal processor (DSP), etc.), system memory component 706 (e.g., RAM), static storage component 708 (e.g., ROM), disk drive component 710 (e.g., magnetic or optical), network interface component 712 (e.g., modem or Ethernet card), display component 714 (e.g., cathode ray tube (CRT) or liquid crystal display (LCD)), input component 716 (e.g., keyboard), cursor control component 718 (e.g., mouse or trackball), and image capture component 720 (e.g., analog or digital camera). In one implementation, disk drive component 710 may comprise a database having one or more disk drive components.

In accordance with embodiments of the present disclosure, computer system 700 performs specific operations by the processor 704 executing one or more sequences of one or more instructions contained in system memory component 706. Such instructions may be read into system memory component 706 from another computer readable medium, such as static storage component 708 or disk drive component 710. In other embodiments, hard-wired circuitry may be used in place of (or in combination with) software instructions to implement the present disclosure. In some embodiments, the various components of the OCT imaging system 110, the health status identification system 101, the model 132, etc., may be in the form of software instructions that can be executed by the processor 704 to automatically perform context-appropriate tasks on behalf of a user.

Logic may be encoded in a computer readable medium, which may refer to any medium that participates in providing instructions to the processor 704 for execution. Such a medium may take many forms, including but not limited to, non-volatile media and volatile media. In one embodiment, the computer readable medium is non-transitory. In various implementations, non-volatile media includes optical or magnetic disks, such as disk drive component 710, and volatile media includes dynamic memory, such as system memory component 706. In one aspect, data and information related to execution instructions may be transmitted to computer system 700 via a transmission media, such as in the form of acoustic or light waves, including those generated during radio wave and infrared data communications. In various implementations, transmission media may include coaxial cables, copper wire, and fiber optics, including wires that comprise bus 702.

Some common forms of computer readable media include, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read. These computer readable media may also be used to store the programming code for the OCT imaging system 110, the health status identification system 101, the model 132, etc., discussed above.

In various embodiments of the present disclosure, execution of instruction sequences to practice the present disclosure may be performed by computer system 700. In various other embodiments of the present disclosure, a plurality of computer systems 700 coupled by communication link 722 (e.g., a communications network, such as a LAN, WLAN, PTSN, and/or various other wired or wireless networks, including telecommunications, mobile, and cellular phone networks) may perform instruction sequences to practice the present disclosure in coordination with one another.

Computer system 700 may transmit and receive messages, data, information and instructions, including one or more programs (i.e., application code) through communication link 722 and communication interface 712. Received program code may be executed by computer processor 704 as received and/or stored in disk drive component 710 or some other non-volatile storage component for execution. The communication link 722 and/or the communication interface 712 may be used to conduct electronic communications between the OCT imaging system 110, and the health status identification system 101, for example.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as computer program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein. It is understood that at least a portion of the OCT imaging system 110, the health status identification system 101, the model 132, etc., may be implemented as such software code.

VII. Definitions

The disclosure is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

Where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

The term "subject" may refer to a subject of a clinical trial, a person or animal undergoing treatment, a person or animal undergoing anti-cancer therapies, a person or animal being monitored for remission or recovery, a person or animal undergoing a preventative health analysis (e.g., due to their medical history), or any other person or patient or animal of interest. In various cases, "subject" and "patient" may be used interchangeably herein.

The term "OCT image" may refer to an image of a tissue, an organ, etc., such as a retina, that is scanned or captured using optical coherence tomography (OCT) imaging technology. The term may refer to one or both of 2D "slice" images and 3D "volume" images. When not explicitly indicated, the term may be understood to include OCT volume images.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those well-known and commonly used in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "about" used with respect to numerical values or parameters or characteristics that can be expressed as numerical values means within ten percent of the numerical values. For example, "about 50" means a value in the range from 45 to 55, inclusive.

The term "ones" means more than one.

As used herein, the term "plurality" can be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, a "model" may include one or more algorithms, one or more mathematical techniques, one or more machine learning (ML) algorithms, or a combination thereof.

As used herein, "machine learning" may include the practice of using algorithms to parse data, learn from it, and then make a determination or prediction about something in the world. Machine learning uses algorithms that can learn from data without relying on rules-based programming.

As used herein, an "artificial neural network" or "neural network" may refer to mathematical algorithms or computational models that mimic an interconnected group of artificial neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network may process information in two ways; when it is being trained (e.g., using a training dataset) it is in training mode and when it puts what it has learned into practice (e.g., using a test dataset) it is in inference (or prediction) mode. Neural networks may learn through a feedback process (e.g., backpropagation) which allows the network to adjust the weight factors (modifying its behavior) of the individual nodes in the intermediate hidden layers so that the output matches the outputs of the training data. In other words, a neural network may learn by being fed training data (learning examples) and eventually learns how to reach the correct output, even when it is presented with a new range or set of inputs.

VIII. Recitations of Exemplary Embodiments

Embodiment 1. A method, comprising: receiving an optical coherence tomography (OCT) volume image of a retina of a subject; generating, via a deep learning model, a health indication output using the OCT volume image in which the health indication output indicates a level of association between the OCT volume image and a selected health status category for the retina; and generating a map output for the deep learning model using a saliency mapping algorithm, wherein the map output indicates a level of contribution of a set of regions in the OCT volume image to the health indication output generated by the deep learning model.

Embodiment 2. The method of embodiment 1, wherein the selected health status category is a selected stage of age-related macular degeneration and wherein the health indication output is a probability that the OCT volume image evidences the selected stage of age-related macular degeneration.

Embodiment 3. The method of embodiment 2, wherein the selected stage of age-related macular degeneration includes nascent geographic atrophy.

Embodiment 4. The method of any one of embodiments 1-3, wherein the selected health status category represents either a current health status with respect to a time at which the OCT volume image was generated or a future health status predicted to develop within a selected period of time after the time at which the OCT volume image was generated.

Embodiment 5. The method of any one of embodiments 1-4, wherein the saliency mapping algorithm comprises a gradient-weighted class activation mapping (Grad-CAM) algorithm and wherein the map output visually indicates the level of contribution of the set of regions in the OCT volume image to the health indication output generated by the deep learning model.

Embodiment 6. The method of any one of embodiments 1-5, wherein the OCT volume image comprises a plurality of OCT slice images that are two-dimensional and further comprising: generating an evaluation recommendation based on at least one of the health indication output or the map output, wherein the evaluation recommendation identifies a subset of the plurality of OCT slice images for further review.

Embodiment 7. The method of embodiment 6, wherein the subset includes fewer than 5% of the plurality of OCT slice images.

Embodiment 8. The method of any one of embodiments 1-7, further comprising: identifying a set of biomarkers in the OCT volume image for the selected health status category using the map output.

Embodiment 9. The method of embodiment 8, wherein the identifying comprises: identifying a potential biomarker region in association with a region of the set of regions indicated as being associated with the selected health status category; generating a scoring metric for the potential biomarker region; and identifying the potential biomarker region as including at least one biomarker for the selected health status category when the scoring metric meets a selected threshold.

Embodiment 10. The method of embodiment 9, wherein the scoring metric comprises at least one of a size of the potential biomarker region or a confidence score for the potential biomarker region.

Embodiment 11. The method of any one of embodiments 1-9, wherein generating the map output comprises: generating a saliency map for an OCT slice image of the OCT volume image using the saliency mapping algorithm, the saliency map indicating a degree of importance of each pixel in the OCT slice image for the selected health status category; filtering the saliency map to generate a modified saliency map; and overlaying the modified saliency map on the OCT slice image to generate the map output.

Embodiment 12. The method of any one of embodiments 1-11, further comprising: generating a treatment recommendation for the retina based on the health indication output.

Embodiment 13. The method of any one of embodiments 1-12, wherein generating, via the deep learning model, the health indication output comprises: generating an initial output for each OCT slice image of a plurality of OCT slice images that form the OCT volume image to form a plurality of initial outputs; averaging the plurality of initial outputs to form the health indication output.

Embodiment 14. A method comprising: receiving an optical coherence tomography (OCT) volume image of a retina of a subject; generating, via a deep learning model, a health indication output using the OCT volume image in which the health indication output indicates a level of association between the OCT volume image and a selected health status category for the retina; and generating a saliency volume map for the OCT volume image using a saliency mapping algorithm, wherein the saliency volume map indicates a level of contribution of a set of regions in the OCT volume image to the health indication output generated by the deep learning model; and detecting a set of biomarkers in the OCT volume image for the selected health status category using the saliency volume map.

Embodiment 15. The method of embodiment 14, wherein the detecting comprises: filtering the saliency volume map to generate a modified saliency volume map, wherein the modified saliency volume map identifies a set of regions that have at least a threshold contribution to the health indication output generated by the deep learning model; and identifying a potential biomarker region in association with a region of the set of regions; generating a scoring metric for the potential biomarker region; and identifying the potential biomarker region as including at least one biomarker in the set of biomarkers when the scoring metric meets a selected threshold.

Embodiment 16. The method of embodiment 14 or embodiment 15, wherein the selected health status category is a selected stage of age-related macular degeneration and wherein the health indication output is a probability that the OCT volume image evidences the selected stage of age-related macular degeneration.

Embodiment 17. A system, comprising: a non-transitory memory; and a hardware processor coupled with the non-transitory memory and configured to read instructions from the non-transitory memory to cause the system to:
receive an optical coherence tomography (OCT) volume image of a retina of a subject;
generate, via a deep learning model, a health indication output using the OCT volume image in which the health indication output indicates a level of association between the OCT volume image and a selected health status category for the retina; and
generate a map output for the deep learning model using a saliency mapping algorithm, wherein the map output indicates a level of contribution of a set of regions in the OCT volume image to the health indication output generated by the deep learning model.

Embodiment 18. The system of embodiment 17, wherein the selected health status category is a selected stage of age-related macular degeneration and wherein the health indication output is a probability that the OCT volume image evidences the selected stage of age-related macular degeneration.

Embodiment 19. The system of embodiment 17 or embodiment 18, wherein the selected health status category represents either a current health status with respect to a time at which the OCT volume image was generated or a future health status predicted to develop within a selected period of time after the time at which the OCT volume image was generated.

Embodiment 20. The system of any one of embodiments 17-19, wherein the saliency mapping algorithm comprises a gradient-weighted class activation mapping (Grad-CAM) algorithm and wherein the map output visually indicates the level of contribution of the set of regions in the OCT volume image to the health indication output generated by the deep learning model.

Embodiment 21. The system of any one of embodiments 17-20, wherein the OCT volume image comprises a plurality of OCT slice images that are two-dimensional and wherein the hardware processor is further configured to read instructions from the non-transitory memory to cause the system to generate an evaluation recommendation based on at least one of the health indication output or the map output, wherein the evaluation recommendation identifies a subset of the plurality of OCT slice images for further review, the subset including fewer than 5% of the plurality of OCT slice images.

IX. Additional Considerations

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

What is claimed is:

1. A method, comprising:
   receiving an optical coherence tomography (OCT) volume image of a retina of a subject;
   generating, via a deep learning model, a health indication output using the OCT volume image in which the health indication output indicates a level of association between the OCT volume image and a selected health status category for the retina;
   generating a map output for the deep learning model using a saliency mapping algorithm, wherein the map output indicates a level of contribution of a set of regions in the OCT volume image to the health indication output generated by the deep learning model;
   identifying a set of biomarkers in the OCT volume image for the selected health status category using the map output, comprising:
      identifying, using a bounding shape, a potential biomarker region in association with a region of the set of regions indicated as being associated with the selected health status category;
      generating a scoring metric for the potential biomarker region; and
      identifying the potential biomarker region as including at least one biomarker for the selected health status category when the scoring metric meets a selected threshold; and
   generating a biomarker map, wherein the biomarker map comprises the bounding shape and the scoring metric overlaid on the OCT volume image.

2. The method of claim 1, wherein the selected health status category is a selected stage of age-related macular degeneration and wherein the health indication output is a probability that the OCT volume image evidences the selected stage of age-related macular degeneration.

3. The method of claim 2, wherein the selected stage of age-related macular degeneration includes nascent geographic atrophy.

4. The method of claim 1, wherein the selected health status category represents either a current health status with respect to a time at which the OCT volume image was generated or a future health status predicted to develop within a selected period of time after the time at which the OCT volume image was generated.

5. The method of claim 1, wherein the saliency mapping algorithm comprises a gradient-weighted class activation mapping (Grad-CAM) algorithm and wherein the map output visually indicates the level of contribution of the set of regions in the OCT volume image to the health indication output generated by the deep learning model.

6. The method of claim 1, wherein the OCT volume image comprises a plurality of OCT slice images that are two-dimensional and further comprising:
   generating an evaluation recommendation based on at least one of the health indication output or the map output, wherein the evaluation recommendation identifies a subset of the plurality of OCT slice images for further review, the subset including fewer than 5% of the plurality of OCT slice images.

7. The method of claim 1, wherein the scoring metric comprises at least one of a size of the potential biomarker region or a confidence score for the potential biomarker region.

8. The method of claim 1, wherein generating the map output comprises:
   generating a saliency map for an OCT slice image of the OCT volume image using the saliency mapping algorithm, the saliency map indicating a degree of importance of each pixel in the OCT slice image for the selected health status category;
   filtering the saliency map to generate a modified saliency map; and
   overlaying the modified saliency map on the OCT slice image to generate the map output.

9. The method of claim 1, further comprising:
   generating a treatment recommendation for the retina based on the health indication output.

10. The method of claim 1, wherein generating, via the deep learning model, the health indication output comprises:
   generating an initial output for each OCT slice image of a plurality of OCT slice images that form the OCT volume image to form a plurality of initial outputs; and
   averaging the plurality of initial outputs to form the health indication output.

11. A method comprising:
   receiving an optical coherence tomography (OCT) volume image of a retina of a subject;
   generating, via a deep learning model, a health indication output using the OCT volume image in which the health indication output indicates a level of association between the OCT volume image and a selected health status category for the retina; and
   generating a saliency volume map for the OCT volume image using a saliency mapping algorithm, wherein the saliency volume map indicates a level of contribution of a set of regions in the OCT volume image to the health indication output generated by the deep learning model;
   detecting a set of biomarkers in the OCT volume image for the selected health status category using the saliency volume map, comprising:

identifying, using a bounding shape, a potential bio-marker region in association with a region of the set of regions indicated as being associated with the selected health status category;

generating a scoring metric for the potential biomarker region; and identifying the potential biomarker region as including at least one biomarker for the selected health status category when the scoring metric meets a selected threshold; and generating a biomarker map, wherein the biomarker map comprises the bounding shape overlaid on the OCT volume image.

12. The method of claim 11, wherein the selected health status category is a selected stage of age-related macular degeneration and wherein the health indication output is a probability that the OCT volume image evidences the selected stage of age-related macular degeneration.

13. A system, comprising:

a non-transitory memory; and a hardware processor coupled with the non-transitory memory and configured to read instructions from the non-transitory memory to cause the system to:

receive an optical coherence tomography (OCT) volume image of a retina of a subject;

generate, via a deep learning model, a health indication output using the OCT volume image in which the health indication output indicates a level of association between the OCT volume image and a selected health status category for the retina;

generate a map output for the deep learning model using a saliency mapping algorithm, wherein the map output indicates a level of contribution of a set of regions in the OCT volume image to the health indication output generated by the deep learning model;

identify a set of biomarkers in the OCT volume image for the selected health status category using the map output, comprising:

identify, using a bounding shape, a potential biomarker region in association with a region of the set of regions indicated as being associated with the selected health status category;

generate a scoring metric for the potential biomarker region; and identify the potential biomarker region as including at least one biomarker for the selected health status category when the scoring metric meets a selected threshold; and generate a biomarker map, wherein the biomarker map comprises the bounding shape and the scoring metric overlaid on the OCT volume image.

14. The system of claim 13, wherein the selected health status category is a selected stage of age-related macular degeneration and wherein the health indication output is a probability that the OCT volume image evidences the selected stage of age-related macular degeneration.

15. The system of claim 13, wherein the selected health status category represents either a current health status with respect to a time at which the OCT volume image was generated or a future health status predicted to develop within a selected period of time after the time at which the OCT volume image was generated.

16. The system of claim 13, wherein the saliency mapping algorithm comprises a gradient-weighted class activation mapping (Grad-CAM) algorithm and wherein the map output visually indicates the level of contribution of the set of regions in the OCT volume image to the health indication output generated by the deep learning model.

17. The system of claim 13, wherein the OCT volume image comprises a plurality of OCT slice images that are two-dimensional and wherein the hardware processor is further configured to read instructions from the non-transitory memory to cause the system to generate an evaluation recommendation based on at least one of the health indication output or the map output, wherein the evaluation recommendation identifies a subset of the plurality of OCT slice images for further review, the subset including fewer than 5% of the plurality of OCT slice images.

18. The method of claim 7, wherein the scoring metric comprises the size of the potential biomarker region; and wherein the size of the potential biomarker region is defined by a number of pixels.

*   *   *   *   *